(12) United States Patent
Parissenti et al.

(10) Patent No.: US 7,588,903 B2
(45) Date of Patent: Sep. 15, 2009

(54) USE OF ISOGENIC DRUG-RESISTANT CELL LINES TO DETERMINE THE SEQUENCE OF CHEMOTHERAPEUTIC DRUG TREATMENT

(76) Inventors: Amadeo Parissenti, c/o Northeastern Regional Cancer Centre, 41 Ramsey Lake Road, Sudbury, Ontario (CA) P3E 5J1; Baoqing Guo, c/o Northeastern Regional Cancer Centre, 41 Ramsey Lake Road, Sudbury, Ontario (CA) P3E 5J1; David J. Villeneuve, c/o Northeastern Regional Cancer Centre, 41 Ramsey Lake Road, Sudbury, Ontario (CA) P3E 5J1; Stacey L. Hembruff, c/o Northeastern Regional Cancer Centre, 41 Ramsey Lake Road, Sudbury, Ontario (CA) P3E 5J1

( * ) Notice: Subject to any disclaimer, the term of this patent is extended or adjusted under 35 U.S.C. 154(b) by 338 days.

(21) Appl. No.: 10/580,507

(22) PCT Filed: Nov. 26, 2004

(86) PCT No.: PCT/CA2004/002039
§ 371 (c)(1),
(2), (4) Date: May 23, 2006

(87) PCT Pub. No.: WO2005/052184
PCT Pub. Date: Jun. 9, 2005

(65) Prior Publication Data
US 2007/0254330 A1 Nov. 1, 2007

Related U.S. Application Data

(60) Provisional application No. 60/525,479, filed on Nov. 26, 2003.

(51) Int. Cl.
C12Q 1/04 (2006.01)
(52) U.S. Cl. .......................... 435/7.23; 435/4
(58) Field of Classification Search ................. 435/7.23, 435/4
See application file for complete search history.

(56) References Cited

U.S. PATENT DOCUMENTS 6,664,288 B1 12/2003 Pardee et al.
6,875,745 B2 4/2005 Pardee et al.

FOREIGN PATENT DOCUMENTS

CA 2 369 303 A1 10/2000

OTHER PUBLICATIONS

Alli et al. 2002. Effect of Stathmin on the Sensitivity to Antimicrotubule Drugs in Human Breast Cancer, Cancer Research, vol. 62, pp. 6864-6869.* http://www.google.com/search? Google+Search&aq=f&oq=, Printed Nov. 21, 2008.*
Wikipedia, http://en.wikipedia.org/wiki/camptothecin, Printed Nov. 19, 2008.*
Crown, John, Nonanthracycline Containing Docetaxel-Based Combinations in Metastatic Breast Cancer, The Oncologist 2001:6 (suppl 3): pp. 17-21, AlphaMed Press.
L. Austin Doyle, et al., A Multidrug Resistance Transporter From Human MCF-7 Breast Cancer Cells, Prac. Natl. Acad. Sci., vol. 95, pp. 15665-15670, Dec. 1998.
Douglas D. Ross, et al., Atypical Multidrug Resistance: Breast Cancer Resistance Protein Messenger RNA Expression in Mitoantrone-Selected Cell Lines, Journal of the National Cancer Institute, vol. 91, No. 5, Mar. 3, 1999.
Eswaran Devarajan, et al., Human Breast Cancer MCF-7 Cell Line Contains Inherently Drug-Resistant Subclones With Distinct Genotypic and Phenotypic Features, International Journal of Oncology 20: pp. 913-920, 2002.
Erin L. Volk, et al., Methotrexate Cross-Resistance in a Mitoxantrone-selected Multidrug-Resistant MCF-7 Breast Cancer Cell Line Is Attributable to Enhanced Energy-Dependent Drug Efflux, Cancer Research 60: pp. 3514-3521, Jul. 1, 2000.
Thomas Litman, et al., The Multidrug-Resistant Phenotype Associated with Overexpression of the New ABC Half-Transporter, MXR (ABCG2), Journal of Cell Science 113, pp. 2011-2021, 2000, Great Britain.
Gen Sheng Wu and Zhenhua Ding, Caspase 9 is Required for p53-Dependent Apoptosis and Chemosensitivity in a Human Ovarian Cancer Cell Line, Oncogene 21, pp. 1-8, 2002.
Baoqing Guo, et al., Potent Killing of Paclitaxel and Doxorubicin-Resistant Breast Cancer Cells By Calphostin C Accompanied by Cytoplasmic Vacuolization, Breast Cancer Research and Treatment 82: pp. 125-141, 2003, Netherlands.
Soo-Jung Park, et al., A P-glycoprotein and MRP1-Independent Doxorubicin-Resistant Variant of the MCF-7 Breast Cancer Cell Line with Defects in Capase-6, -7, -8, -9 and -10 Activation Pathways, Anticancer Research 24: pp. 123-132, 2004.
Kostas V. Floros, et al., mRNA Expression Analysis of a Variety of Apoptosis-Related Genes, Including the Novel Gene of the BCL2-Family, BCL2L12, in HL-60 Leukemia Cells After Treatment with Carboplatin and Doxorubicin, Biol. Chem., vol. 385, pp. 1099-1103, Nov. 2004, Berlin, NY.

(Continued)

Primary Examiner—Jon P Weber
Assistant Examiner—Kailash C Srivastava
(74) Attorney, Agent, or Firm—Brinks Hofer Gilson & Lione

(57) ABSTRACT

The present invention provides a method for determining a sequence to administer multiple types of chemotherapeutic drugs for killing cancerous cells to reduce the induction of drug cross-resistance in a patient. The methods also involves screening drug candidates to select a lead anticancer drug from amongst a plurality of candidate drugs, the lead having a reduced capacity to induce cross resistance in a patient against one or more known anticancer drugs, and all of the drugs having the ability to kill cancerous cells of the same selected tumour type. Moreover, the methods involve determining a sequence to administer multiple types of cytotoxic drugs for killing undesired cells to reduce the induction of drug cross-resistance in the cells.

11 Claims, 10 Drawing Sheets

OTHER PUBLICATIONS

Ching-Huang Wu, et al., β2-Microglobulin Induces Apoptosis in HL-60 Human Leukemia Cell Line and Its Multidrug Resistant Variants Overexpressing MRP1 but Lacking Bax or Overexpressing P-glycoprotein, Oncogene 20, pp. 7006-7020, 2001.

Tamara Minko, et al., Preliminary Evaluation of Caspases-Dependent Apoptoiss signaling Pathways of Free and HPMA Copolymer-Bound Doxorubicin in Human Ovarian Carcinoma Cells, Journal of Controlled Release 71, pp. 227-237, 2001.

* cited by examiner

USE OF ISOGENIC DRUG-RESISTANT CELL LINES TO DETERMINE THE SEQUENCE OF CHEMOTHERAPEUTIC DRUG TREATMENT

BENEFIT OF EARLIER APPLICATION

This application claims priority to PCT/CA2004/002039 filed Nov. 26, 2004, which claims priority to U.S. Provisional Application Ser. No. 60/525,479 filed Nov. 26, 2003.

FIELD OF THE INVENTION

The invention relates to the fields of biology and treatment of cancer patients, specifically cancer patients with tumor cells that develop resistance to certain chemotherapeutic drugs.

BACKGROUND OF THE INVENTION

Treatment of cancer by chemotherapy frequently involves the use of a sequence of drugs, with the treating physician switching the treatment regime from one drug to another as resistance to each drug builds in turn. Failure of treatment can arise as a result of cross-resistance wherein a patient develops resistance to a first drug which in turn will generate resistance to treatment by a second drug. For example, in the treatment of breast cancer such cross resistance is often encountered when using the commonly-used drugs in the anthracycline and taxane families.

Doxorubicin (Adriamycin™) and paclitaxel (Taxol™) are both very effective agents used in the treatment of breast cancer. The former drug is an anthracycline which disrupts the uncoiling of DNA by topoisomerase II, intercalates between DNA strands, and causes DNA lesions, thereby interfering with DNA replication preferentially in rapidly dividing tumor cells. Doxorubicin can also kill tumor cells by stimulating Fas-mediated apoptosis through the induction of Fas ligand expression. Paclitaxel is a taxane which interferes with microtubule depolymerization in tumor cells resulting in an arrest of the cell cycle in mitosis followed by the induction of apoptosis. Adjuvant chemotherapy with anthracyclines and/or taxanes is now standard for treatment of breast cancer in lymph node positive women and in women with inflammatory breast cancer.

Despite their effectiveness, tumor resistance to paclitaxel or doxorubicin often develops, resulting in the failure of chemotherapy. Fewer than one-half of breast cancer patients respond to paclitaxel after failing anthracycline chemotherapy. A number of mechanisms have been identified by which resistance to doxorubicin can occur in tumor cells in vitro. These include the induction of drug transporters (both P-glycoprotein-P-gp, type ABCB1) and the multidrug resistance protein (MRP, type ABCC1), the down-regulation of topoisomerase II a activity, mutations in p53 activity, a disruption in the ability of doxorubicin to induce apoptosis, and the increased synthesis of both thymidylate synthase and the drug-conjugating enzyme glutathione-S-transferase. Similarly, resistance to paclitaxel in tumour cells in vitro can occur via a variety of mechanisms. These include the induction of P-gp expression, the acquisition of mutations in the α and β chains of tubulin, amplification of the serine-threonine kinase AURORA-A, cellular elevations in p53 levels, suppression of JNK-mediated Bcl-xL phosphorylation, downregulation of Bcl-2 (which binds paclitaxel), and upregulation of the Akt (PI-3-kinase) pathway.

Since paclitaxel is a very effective drug for the treatment of breast cancer and has a low toxicity profile relative to doxorubicin (when used in combination with granulocyte colony stimulating factor), breast cancer patients may be better served by treatment with paclitaxel before the administration of anthracyclines such as doxorubicin. This difference in tumor drug responsiveness in second-line chemotherapy may be related to differences in the capacities of paclitaxel and doxorubicin to induce cross-resistance to each other and possibly to other drugs. For example, longterm exposure of breast tumor cells to doxorubicin (resulting in resistance to the drug) may induce strong cross-resistance to paclitaxel, while similar exposure to paclitaxel may have less effect on doxorubicin cytotoxicity.

In general, there is a need for a method to determine the sequence of administration of chemotherapeutic drugs to minimize the possibility of cross-resistance. While empirical studies may be conducted to determine this, it is of course preferable to provide an in vitro approach that will accurately predict patient outcomes. This is particularly the case when it comes to determining the sequence of administration of three or more drugs, giving rise a large number of permutations and thus empirical testing becomes essentially impossible.

SUMMARY OF THE INVENTION

It is an object of the present invention to provide an improved method to determine a sequence of administration of chemotherapeutic drugs, in which the method involves in vitro determination of the possibility of cross-resistance between drugs. It is a further object to provide a screening method to identify a drug candidate which demonstrates reduced capacity to induce cross-resistance against other anticancer drugs in a patient.

It was the discovery of the present inventor that a panel of isogenic cell cultures may be provided, comprising a plurality of strains each selected for resistance to a selected drug, as well as the parent strain which retains sensitivity to all of the selected drugs. Using this panel, one may determine a suitable sequence of application of chemotherapeutic drugs. The method comprises exposing a strain that has been selected for resistance to a first drug ("drug A") to a second drug ("drug B"). In a reciprocal manner, one assesses the sensitivity to drug A for an isogenic strain of cells selected for resistance to drug B. If the killing action of drug B is little compromised by selection for resistance to drug A, while cells resistant to drug B have strong cross resistance to drug A, then the order of application should be drug A followed by drug B. The same method may used to determine the sequence of application of three drugs by raising three independent isogenic cell lines resistant to each drug (as well as the parent strain) and monitoring sensitivity to all of the drugs used in the study. The drug eliciting the least cross resistance to the other drugs in the screen is placed first in the order, while the drug inducing the strongest cross resistance to other drugs is placed last. While drug efficacy should also be a consideration in determining drug order, this method may prove highly useful in guiding the order of drug administration. The relative ease with which such panels may be generated and such testing applied renders it reasonably simple to carry out a large number of tests. It is important in this approach that the drug-resistant cells raised are collections of cells (rather than single clones) and are isogenic to avoid differences in cell sensitivity due to "clonal variation" amongst cells or the isolation of a rare variant in the cell population.

The information generated in the testing methodology described above has various uses. It may used to inform treating physicians about appropriate therapeutic methods. The information may be used in the drug approval process, or by pharmaceutical manufacturers in determining the effectiveness of therapeutic agents. The method may also be used to provide a customized treatment methodology for an individual patient, if the multistrain isogenic cell line used for the test is derived from the patient's tumor. Moreover, this approach (or a variation thereof) could be used: a) to determine drug order for the treatment any disease where cytotoxic drugs are used for treatment, or b) in a screen of multiple structural permutations of a given drug to identify the form which elicits minimal cross resistance to other drugs used in the screen.

While the present invention has been tested with a cell line and drugs related to breast cancer, the invention is not limited to this form of cancer. Rather, the methods disclosed and claimed herein apply with suitable modification to any form of cancer that is susceptible to treatment by chemotherapy comprising multiple drugs. Moreover, this approach could be used to determine drug order for the optimal treatment of any disease where cytotoxic drugs are used, as well as the selection of promising drug candidates in a screen.

In one aspect, the invention comprises a method of determining the sequence of administering multiple types of selected chemotherapeutic drugs for killing cancerous cells, comprising the steps of:

(a) preparing a panel of isogenic cell lines from the same tumor type as said cancerous cells; the cell lines consist of a first control population which is sensitive to all of the selected drugs and a plurality of populations (each comprising a cell line) each of which is resistant to a separate chemotherapeutic drug effective against the tumor type; all cells within the panel being isogenic;

(b) assessing the sensitivity of each of said drug-resistant cell strains to all drugs used in (a) relative to the drug-sensitive parental cell line. This results in the generation of a "resistance factor". For example, if a paclitaxel-resistant cell line requires 40-fold more paclitaxel than the drug-sensitive parent to kill 50% of cells, then the resistance factor for the paclitaxel resistant cell line is 40.

(c) creation of an X by Y "cross resistance array", where X represents the resistance factors for each of said drug-resistant cell lines created and Y represents the various drugs examined for their cytotoxic capacity. Typically, X and Y represent the same value. A possible example of a screen of drugs A, B, and C using the above approach might yield the following data:

| | RESISTANCE FACTOR FOR DRUG | | |
| --- | --- | --- | --- |
| | Cell Line Resistant to Drug A | Cell Line Resistant to Drug B | Cell Line Resistant to Drug C |
| Drug A | 40 | 4000 | 1.5 |
| Drug B | 4 | 50 | 1.5 |
| Drug C | 3 | 2 | 8 |

(d) determining drug order using the resistance factor information. The drug which generates a drug-resistant cell line with little cross resistance to other drugs is placed first, while the drug which generates a drug-resistant cell line with strong cross resistance to a variety of drugs is placed last. For the above example, the optimum order of drug administration would be C followed by A followed by B.

This process could also be used in a screen of drug candidates, for example where various structural permutations of a specific drug ($A_a$ to $A_n$) could be assessed for the structure which permits minimal cross resistance when used in combination with one or more known anticancer drugs B and C. Thus in one aspect, the invention is a method of screening drug candidates to select a first anticancer drug having a reduced capacity to induce cross resistance against a second anticancer drug in a patient, said first and second drugs both having the ability to kill cancerous cells of a selected tumor type. In this aspect, the method comprises the steps of providing a plurality of drug candidates and one or more known anticancer drugs; providing a panel of isogenic strains in the manner described above, in which the strains are resistant to the candidate drugs, as well as the one or more of the known anticancer agents; and determining a lead candidate as the drug which corresponds to the strain which demonstrates the least resistance to the others of said drugs. The method for making this determination is the same as that described above.

Preferably, the above method is used to select a lead candidate drug from amongst a plurality of related candidate drugs, such as one or more of structural isomers, positional isomers, polymorphic (crystalline or amorphic) forms, chemical analogs, salts, or tautomers of a selected candidate. The lead candidate is selected as the form of the compound having the property of inducing the lease cross-resistance to the one or more known anticancer drugs.

The inventor has also made the discovery that expression of procaspase-9 by a tumor cell is down-regulated in cells which are resistant to certain drugs such as doxorubicin. Hence, the present invention further comprises a method of determining resistance of cancerous cells to killing by an anticancer drug and in particular an anthracycline drug, comprising the step of determining the expression of procaspase-9 or caspase-9 within said cells and identifying said resistance upon determining reduced production of procaspase-9 within said cells. The invention also consists of the use of caspase-9 or procaspase-9 as a medicament or to prepare a medicament to enhance the effectiveness of an anthracycline anticancer drug in a patient resistant to treatment by said anthracycline.

To test this invention, two variants of the MCF-7 breast adenocarcinoma cell line resistant to either doxorubicin or paclitaxel were prepared in the laboratory (MCF-7$_{DOX}$ and MCF-7$_{TAX}$ cells, respectively). Both cell lines originated from the same lot of MCF-7 cells from the American Tissue Culture Collection and were selected for drug resistance in an identical protocol. These drug-resistant cell lines were found to be isogenic by cDNA microarray analysis and are thus ideally suited to an assessment of the pharmacogenomics of doxorubicin and paclitaxel resistance in breast tumor cells.

The inventor compared the sensitivity of MCF-7, MCF-7$_{TAX}$ and MCF-7$_{DOX}$ cells to a variety of chemotherapy drugs to assess the relative capacities of doxorubicin and paclitaxel to induce cross-resistance to each other and to other drugs. Interestingly, it was found that the level of cross-resistance to taxanes (paclitaxel and docetaxel) in MCF-7$_{DOX}$ cells far exceeded the level of cross-resistance to anthracyclines (doxorubicin and epirubicin) exhibited by MCF-7$_{TAX}$ cells. We also observed that this strong cross-resistance correlated with an almost complete block in paclitaxel uptake by MCF-7$_{DOX}$ cells, possibly resulting from an observed increase in the expression of both P-gp and the breast cancer resistance protein. Moreover, we found that procaspase-9 levels are strongly increased by doxorubicin treatment (but not paclitaxel treatment) in breast tumor cells and that the level of this initiator caspase is strongly downregulated in MCF-7$_{DOX}$ cells but not MCF-7$_{TAX}$ cells. Taken together, these studies are consistent with previous clinical findings and provide possible mechanisms to account for the poor response to paclitaxel exhibited by tumors of breast tumor patients following treatment with doxorubicin.

A complete panel of isogenic drug-resistant MCF-7 breast tumor cell lines has been established which should serve as an excellent model system to study changes in gene expression or protein function in cells which accompany resistance to specific drugs.

A complete panel of isogenic drug-resistant MCF-7 breast tumor cell lines has been deposited at The International Depositary Authority of Canada (IDAC) in Winnipeg, Canada under the accession numbers 271104-01 and 271104-02.

Figure 1:
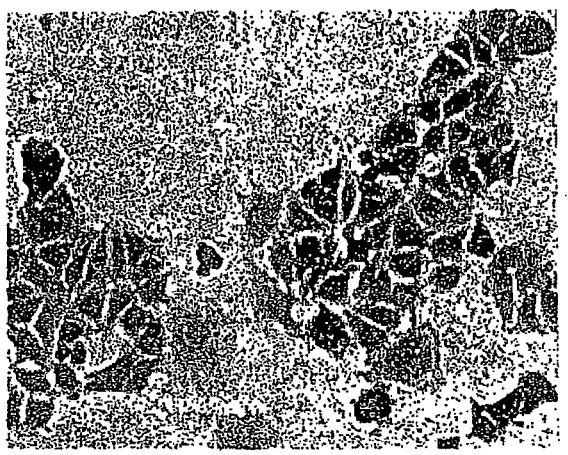
FIG. 1 illustrates the appearance of MCF-7, MCF-7$_{TAX}$, and MCF-7$_{DOX}$ cells after haematoxylin/eosin staining. MCF-7, MCF-7$_{TAX}$, and MCF-7$_{DOX}$ cells were grown on Snowcoat glass slides in H21 medium to 40-50% confluence, fixed in xylene, and subjected to haematoxylin/eosin staining as described in Materials and Methods.
Figure 1:
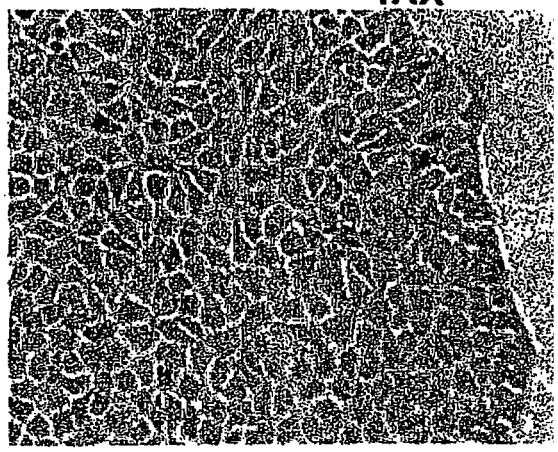
Figure 1:
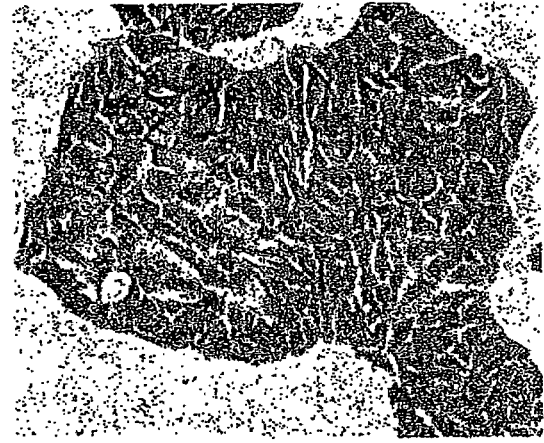

TABLE I represents the morphology, staining, and expression of various tumor marker proteins in MCF-7, MCF-7$_{TAX}$, and MCF-7$_{DOX}$ cells. MCF-7 cells and its paclitaxel- or doxorubicin-resistant counterparts (MCF-7$_{TAX}$ and MCF-7$_{DOX}$ cells, respectively) were grown on Snowcoat™ glass slides in drug-free medium, fixed in ethanol and examined microscopically after various histological staining methods or by immunohistochemistry using antibodies to a variety of tumor marker proteins. The location of the tumor marker proteins was noted. Cellular levels of caspase-3 were as determined by immunoblotting experiment using a monoclonal antibody specific for the pro-form of caspase-3. Identical experiments were also conducted using the doxorubicin-resistant NCI-ADR cell line which is a known, rare, caspase-3-positive variant within the MCF-7 population, which can be obtained upon selection of cells for resistance to doxorubicin.

While the invention will be described in conjunction with the embodiment described in detail, it will be understood that it is not intended to limit the invention to such embodiment. On the contrary, it is intended to cover all alternatives, modifications and equivalents as one skilled in the art would recognize as being included within the scope of the invention as defined by the appended claims.

MATERIALS AND METHODS

Reagents

Drugs used in this study came from a variety of sources. Doxorubicin, epirubicin, 5-fluorouracil, and irinotecan were from Pharmacia and Upjohn Pharmaceuticals, Mississauga, ON. Vinblastine, methotrexate, and cisplatin were from Faulding Canada, Inc., Montreal, QC. The remaining drugs had the following sources: paclitaxel and cyclophosphamide (Bristol Myers Squibb, Montreal, QC), docetaxel (Aventis Pharma, Inc., Laval, QC), and etoposide (Novopharm Pharmaceuticals, Toronto, ON). All drugs were used directly except for irinotecan, where its active metabolite (SN38) was used. The P-gp inhibitor valspodar (also known as AMDRAY™ or PSC-833) was a kind gift from Novartis Pharmaceuticals (Basel, Switzerland).

Propagation of MCF-7 Cells

MCF-7 cells were obtained from the American Tissue Culture Collection (lot HTB-22). The cell lines were grown as a monolayer in 75 cm² tissue culture flasks and maintained in H-21 medium containing L-glutamine and 10% American-sourced fetal bovine serum (FBS; Hyclone Laboratories, Logan, Utah). Cells were grown at 37° C. in a humidified atmosphere containing 5% $CO_2$. Upon reaching confluence, cells were released from their flasks by trypsin/EDTA treatment and 10% of the cells were introduced into new flasks containing identical medium. Cells were allowed a maximum of 15 passages before new cultures were established from frozen stocks.

Establishment of Paclitaxel- and Doxorubicin-Resistant MCF-7 Cell Lines

MCF-7 cells, propagated as described above, were incubated for two weeks with either doxorubicin or paclitaxel at a concentration 1000-fold less than that required to kill 50% of the cells ($IC_{50}$) (9 nM and 0.56 nM, respectively). Twice weekly, nonadherent (dead) cells were removed by discarding the existing medium and replacing it with fresh, drug-containing medium. Once confluence was achieved (usually 1 week), cells were released from their flasks by trypsin/EDTA treatment and reseeded into flasks. At the end of the two-week period, all remaining viable cells were released by trypsinization, diluted 10-fold into PBS, and harvested by centrifugation. The cells were resuspended in fresh H-21 medium, with several aliquots removed for storage and future analysis. The remaining cells were incubated with drug at a concentration 3-fold higher than the previous dose. Nonadherent dead cells were again removed as described above and the process repeated until a drug dose was reached where all cells in the population were killed. Cells that grew at the maximally-tolerated drug concentrations were deemed to be "terminally selected". The maximally-tolerated drug doses during the selection process were 0.3 μM and 6.6 nM for doxorubicin and paclitaxel, respectively. All experiments described in this study were derived from frozen stocks of terminally selected MCF-7$_{TAX}$ and MCF-7$_{DOX}$ cells.

Treatment of Cells with the P-gp Inhibitor Valspodar

In some experiments, MCF-7, MCF-7$_{TAX}$ and MCF-7$_{DOX}$ cells were treated for one hour at 37° C. with 2 μM valspodar, a highly effective inhibitor of P-gp. After the one hour incubation, the culture medium was removed and the cells washed free of valspodar using PBS. Cells were then re-introduced into valspodar-free culture medium containing FBS (with or without chemotherapy drugs). Stock concentrations of valspodar were prepared in drug solubilization solution [10% Tween20, 40% ethanol]. Control cells lacking valspodar were treated with an equivalent amount of drug solubilization solution under identical conditions. Two μM valspodar was the maximum amount of valspodar which could be added to MCF-7 cells, without inducing significant cytotoxicity. MCF-7$_{TAX}$ and MCF-7$_{DOX}$ cells could tolerate up to 10 μM valspodar, without resulting in cell killing. Thus, the concentration of valspodar used in some experiments was increased to 10 μM.

Histological and Immunohistochemical Characterization of MCF-7$_{TAX}$ and MCF-7$_{DOX}$ Cells Cells from frozen stocks of terminally selected MCF-7$_{TAX}$ and MCF-7$_{DOX}$ cells were propagated in several tissue culture plates containing Snowcoat™ microscope glass slides (Surgipath Laboratories, Winnipeg, MB). Cells were grown to approximately 70% confluence, fixed in methanol, and subjected to a variety of staining procedures using a Leica Autostainer XL Automatic Slide Stainer. Fixed cells were subjected to haematoxylin/eosin staining as described previously or immunohistochemical staining using a standard protocol and a variety of antibodies to tumor marker proteins. These included antibodies to μ1 antichymotrypsin (polyclonal), carcinoembryonic antigen (clone TF-3H8-1), cytokeratin 7 (clone K72), cytokeratin 20 (clone KS20.8), a wide spectrum of keratins (clones AE1 to AE3), low molecular weight keratins (clone 5D3), vimentin (clone 3B4), epithelial membrane antigen (Mc5), the S100 protein (polyclonal), the estrogen receptor (clone 6F11), the progesterone receptor (clone 1A6), p53 (clone Bp53-11), and Bcl-2 (clone 100/05). All antibodies were from Ventana Medical Supplies (Tucson, Ariz.), except for the wide spectrum keratin antibody, which was from DakoCytomation (Mississauga, ON). The subcellular location and expression level of these proteins were determined by the location and intensity of staining of peroxidase substrates as viewed by the experimenter.

Clonogenic Assays for Measurement of Cellular Sensitivity to Drugs

MCF-7, MCF-7$_{TAX}$, and MCF-7$_{DOX}$ cells were measured for their sensitivity to a variety of drugs using a clonogenic assay which assesses the ability of cells to form large colonies of actively dividing cells in a semi-solid medium after a 24 hour treatment with drug. Briefly, 5 ml of H21 medium with 10% fetal bovine serum was introduced into 12 tissue culture flasks (25 cm² area) and each flask seeded with $2.5 \times 10^5$ cells. The cells were allowed to adhere overnight, after which they were incubated for 24 h with varying amounts of drug with or without pretreatment with valspodar (as described above). After the incubation period, the medium was removed and the floating cells collected by centrifugation. The remaining adherent cells were released from their flasks by trypsin treatment, combined with the nonadherent cells, washed in 5 ml of H21 medium containing FBS pelleted, and resuspended in 300 μl of the same medium. The cellular suspension was then added to 2.7 ml of methylcellulose solution [70 ml of 2.6% methylcellulose (w/v in IMDM medium) (Sargent Welch Laboratories, Buffalo Grove, Ill.) and 30 ml of FBS]. Each sample was vortexed vigorously for 10 s to ensure even distribution of cells within the viscous medium. 1.2 ml of each cellular suspension were placed into 6 well plates and incubated for a minimum of one week at 37° C./5% $CO_2$ until large colonies of cells were visible. The number of viable colonies within 5 randomly selected fields was then scored by light microscopy and expressed as a percentage of colonies found for control cells in the absence of drug.

Measurement of [³H]-Paclitaxel and [¹⁴C]-5-Fluorouracil Accumulation into Cells

To monitor cellular accumulation of paclitaxel, MCF-7, MCF-7$_{TAX}$ and MCF-7$_{DOX}$ cells were seeded into 6-well plates at a concentration of $1.0 \times 10^5$ cells per well in 3 ml of H21/FBS medium. After propagation in culture for 1 day, the cells were incubated with or without valspodar (as described above). The medium surrounding the cells was then removed, and the cells washed twice with 5 ml of fresh H21/FBS medium. After the washing steps, cells were incubated with 3 ml of fresh medium containing [$^3$H]-paclitaxel or [$^{14}$C]-5-Fluorouracil (Moravek Biochemicals, Brea, Calif.) at concentrations near the $IC_{50}$ for each drug (10 nM and 1 µM respectively). The cells in each well were then incubated at 37° C. for varying times (from 0-24 h). At specific time points, the medium was removed from a representative well and the cells washed twice with 3 ml aliquots of ice-cold PBS. Cells were then released from their wells by trypsin treatment and placed in scintillation vials. After addition of Scintiverse E cocktail (Mandel Scientific, Guelph, ON), the radioactivity associated with the cells was measured using a liquid scintillation counter.

Measurement of Cellular Doxorubicin Uptake by Flow Cytometry

To monitor cellular uptake of doxorubicin, MCF-7, MCF-7$_{TAX}$ and MCF-7$_{DOX}$ cells were prepared as described above (2.0×10$^5$ cells per well) and treated with or without valspodar. After removal of the medium and washing of the cells with 5 ml of H21/FBS medium, cells were incubated with 3 ml of H21/FBS medium containing 2 µM doxorubicin. At various time points (from 0-24 hours), the medium was removed and floating cells were collected by centrifugation. Adherent were then washed twice with PBS, released from their wells by trypsin treatment, combined with the nonadherent cells, washed once in PBS, and resuspended in 0.5 ml of PBS. The amount of fluorescence for 2×10$^4$ cells in each sample (due to the uptake of fluorescent doxorubicin) was then measured immediately using a Beckman Coulter Epics™ Elite flow cytometer. The fluorescence of the cells upon stimulation with an argon-ion laser at 488 nm was measured using a PMT4 625DL filter and plotted against cell number. The mean fluorescence associated with the cells was used to compare between samples.

Measurement of MDR1 Gene (P-gp) Expression by RT-PCR

Two independent preparations of RNA were made for each cell line using an RNAeasy™ kit from Qiagen Laboratories (Mississauga, ON) as per the manufacturer's instructions. The quantity of RNA was determined by measurement of the absorbance of a diluted aliquot of the preparation at a wavelength of 260 nm ($A_{260}$) using a Beckman spectrophotometer. Purity of the RNA obtained was determined by measuring the $A_{260}/A_{280}$ ratio. The quality of the RNA was assessed by visualization after denaturing agarose electrophoresis and staining with ethidium bromide. No evidence of RNA degradation was obtained for any of the preparations by this method. Contaminating DNA in the RNA samples was removed by digestion with DNase I. One µg of RNA was diluted to 10 µl using 10× DNase Buffer (Invitrogen Laboratories, Carlsbad, Calif.) and DEPC-treated $H_2O$. To the diluted preparation, 1 unit of amplification grade DNase I (Invitrogen Laboratories, Carlsbad, Calif.) was then added and digestion allowed to proceed at room temperature for 15 minutes. After this time, 25 mM EDTA was added to terminate the reaction and the sample heated at 65° C. for 10 minutes to remove any residual DNase I activity. The various RNAs within each preparation were then reverse-transcribed to cDNAs using the mouse leukemia virus (MLV) reverse transcriptase (Life Technologies, Burlington, ON). Briefly, 4.7 µl of the previous reaction was diluted to 20 µl with a buffer containing 100 mM DTT, 10 mM deoxyribonucleotide triphosphates, 0.2 µM poly-dT primer, and 40 U of RNase inhibitor (Invitrogen Laboratories, Carlsbad, Calif.). The reaction mixture was heated to at 37° C. for 10 minutes after which 1 µl of MLV was added. After one hour at 37° C., the tubes were heated to 95° C. for 5 minutes. For selective amplification of the MDR1 and glyceraldehyde-3-phosphate dehydrogenase (GAPDH) cDNAs in the samples by PCR, 0.5 ml tubes containing 9.1 µl of the following reagents were set up for each sample: 1.1 mM $MgCl_2$, 0.4 µM GAPDH forward primer (5'-ACCACAGTCCATGCCATCAC-3'), 0.4 µM GAPDH reverse primer (5'-TCCACCACCCTGTTGCT-GTA-3'), 1 µM MDR1 forward primer (5'-GCCTGGCAGCT-GGAAGACAAATACACAAA3'), and 1 µM MDR1 reverse primer (5'-CAGACAGCAGCTG-ACAGTCCAAGMCAG-GACT-3'. After a 94° C. "hot start", 2 µl of each of the above cDNA reactions and 1 µl of Taq polymerase (1 unit) was added to each tube. PCR amplification was then allowed to proceed for 34 cycles with the following reaction parameters: denaturation, 94° C. for 30 seconds; annealing, 55° C. for 60 seconds; and elongation, 72° C. for 120 seconds. An equivalent sample lacking the synthesized cDNA was used as a negative control. The products of all PCR reactions were then resolved by standard agarose gel electrophoresis, followed by visualization of the products under UV light after staining of the gel with 0.5 µg/ml ethidium bromide for 30 minutes (in TBE buffer) followed by destaining in buffer without ethidium bromide for an additional 10 minutes.

Flow Cytometric Analysis of P-gp Cell Surface Levels

For measurement of the amount of P-gp present on the cell surface for each cell line, 2.5×10$^5$ cells were introduced into a 10 cm tissue culture plate and allowed to grow for 48 hours. Cells were then trypsinized, washed twice with PBS, and resuspended in 100 µl of PBS buffer containing 1% BSA (PBA). Five µl of MRK-16 antibody (ID Labs, London, ON) were added, after which the cells were incubated at 4° C. for 60 minutes. After the incubation period, the cells were washed twice in PBA and resuspended in 60 µl of PBA. Two µl of a FITC-conjugated goat anti-mouse secondary antibody (ID Labs, London, ON) were then added and the cells incubated for 30 minutes in the dark at 4° C. After incubation with the secondary antibody, cells were washed twice with PBA, resuspended in 100 µl of 1% paraformaldehyde, and incubated at room temperature for 10 minutes. To each sample, 400 µl of PBA were then added. The fluorescence associated with the bound secondary antibody for each sample was measured using the PMT2 channel of an EPICS Elite flow cytometer (Coulter Electronics, Hialeah, Fla.) equipped with an argon ion laser (emission 488 nm) using a 525 nm band pass filter. Background fluorescence was determined using a sample for each cell line where an isotypic control antibody replaced the primary P-gp antibody.

Preparation of Whole Cell and Membrane Extracts of MCF-7, MCF-7$_{TAX}$, and MCF-7$_{DOX}$ Cells Extraction of proteins from whole cells was performed using RIPA buffer [1% Nonidet P-40, 0.5% sodium deoxycholate, 0.1% SDS, and 1 Complete™ protease inhibitor tablet (Roche Pharmaceuticals, Baie d'Urfe, QC) in 50 ml of PBS]. Prior to use, the RIPA buffer was supplemented with sodium orthovanadate and phenylmethylsulfonyl fluoride at final concentrations of 1 mM and 0.1 mg/ml, respectively. Cultured cells were grown as a monolayer and allowed to reach 70-90% confluence in 10 cm tissue culture plates. Twenty-four hours prior to extraction, some plates of cells were treated with 9 nM doxorubicin or 0.56 nM paclitaxel. After drug treatment, the medium was removed and the cells rinsed twice with PBS. All further steps were carried out on ice to minimize denaturation/proteolysis of the proteins. Chilled RIPA buffer (0.6 ml) was added to each plate, after which the cells were scraped from the plate using a Teflon tape-coated razor blade, and transferred to a 1.5 ml microfuge tube. An additional 0.3 ml of RIPA buffer was added to the plate and the resultant suspension was combined with the lysate. The sample was then passed repeatedly through a 21 gauge needle to lyse the cells and shear any DNA present. The lysates were then incubated on ice for 30 minutes, after which they were clarified by centrifugation at 15,000 g for 20 minutes at 4° C. The supernatants were then removed, mixed well, and aliquots placed in 0.5 ml microfuge tubes and stored at −80° C.

For preparation of membrane extracts, cultured cells were grown on 15 cm tissue culture plates and allowed to reach 70-90% confluence. The plates were then trypsinized, and the contents of 4 plates were added together to obtain sufficient quantities of membrane proteins. The cells were centrifuged at 1000 rpm, and the pellet was resuspended in 4 ml of homogenization buffer containing 8.56 g sucrose, 0.315 g Tris-HCl, 1 ml of 1 mM $MgCl_2$, and 1 Complete™ protease inhibitor tablet per 100 ml of sterile $H_2O$, pH 7.4. The solution was then added to a new 15 ml tube and 1 ml of a 50/50 slurry of acid glass beads was added. Each tube was then vortexed 3 times for 20 seconds each, with a 2 minute incubation on ice between vortexing steps to minimize protein denaturation. After vortexing, the tubes were centrifuged at 1500 rpm for 5 minutes at 4° C. The supernatant was then layered onto 6 ml of gradient buffer (48.61 g sucrose, 0.315 g Tris-HCl, 1 ml of 1 mM $MgCl_2$, and 1 Complete™ protease inhibitor tablet in 100 ml of sterile $H_2O$, pH 7.4), which had been placed in an ultracentrifuge tube. The tube was centrifuged at 17,200 rpm for 30 minutes at 4° C. in a Beckman XL70 ultracentrifuge using an SW41Ti rotor. The interface between the homogenization buffer and the gradient buffer was then collected and placed in a 2.0 ml microfuge tube. To this was added 1 ml of dilution buffer (0.315 g Tris-HCl, 1 ml of 1 mM $MgCl_2$, and 1 Complete™ protease inhibitor tablet in 100 ml of sterile $H_2O$, pH 7.4). The sample was then centrifuged at 16 000 g for 20 minutes at 4° C. The resulting pellet of membrane proteins was then resuspended in 50 µl of RIPA buffer and stored at −80° C.

Immunoblotting Experiments Using Whole Cell and Membrane Extracts

Proteins (50 mg) from whole cell extracts were loaded into each lane of a 10% SDS-polyacrylamide gel, on duplicate gels. After electrophoresis, one of the gels was stained with Coomassie Brilliant Blue R to confirm that similar amounts of protein were loaded on gels. A second gel was electrophoretically transferred to a nitrocellulose membrane and the membrane incubated for one hour in blocking buffer [TBS buffer (20 mM Tris, 150 mM NaCl, pH 7.5) supplemented with 5% skim milk powder] to occupy all remaining protein-binding sites on the membrane. After blocking, the membranes were incubated for 1.5 hours at room temperature with an antibody to either caspase-3 (Santa Cruz Biotechnology, Santa Cruz, Calif., clone E-8), caspase-7 (Pharmingen Laboratories, San Diego, Calif., clone B94-1) or caspase-9 (Santa Cruz Biotechnology, Santa Cruz, Calif., clone C-17). Both antibodies were diluted 1:500 in blocking buffer containing 0.1% Tween 20. The primary antibody was then discarded and the membrane washed exhaustively with TBST (TBS buffer supplemented with 0.1% Tween 20). A secondary antibody [a horseradish peroxidase-conjugated anti-rabbit Ig G antibody (Santa Cruz Biotechnology, Santa Cruz, Calif.) diluted 1:10,000 in blocking buffer supplemented with 0.1% Tween 20] was then incubated with the membrane for 1 hour at room temperature. The membranes were washed in TBST for 20 minutes, followed by 3 washes in TBS buffer for 5 minutes each. The washed membrane was then incubated with ECL chemiluminescence substrates (Amersham/Pharmacia Biotech, Baie d'Urfe, QC) for 1 minute, sealed in plastic pouches, and exposed to Kodak X-OMAT film. The film was then developed, and the band intensities compared for the various lanes. The procedure followed was identical for immunoblotting of membrane extracts to assess cellular levels of the breast cancer resistance protein (BCRP), except that 20 µg of membrane protein were loaded into the wells of gels and membranes were probed with a 1:50 dilution of an anti-BCRP mouse monoclonal antibody (Signet Labs, Dedham, Mass., clone BXP21) and a 1:10,000 dilution of an anti-mouse HRP secondary antibody (Santa Cruz Biotechnology, Santa Cruz, Calif.).

EXAMPLES

Example 1

MCF-7, MCF-7$_{TAX}$, and MCF-7$_{DOX}$ Cells are Isogenic

To assess the capacity of paclitaxel or doxorubicin to induce cross-resistance to each other and to additional chemotherapeutic agents, cell lines resistant to paclitaxel (MCF-7$_{TAX}$) or doxorubicin (MCF-7$_{DOX}$) were prepared. During selection in the presence of increasing concentrations of drug, clonal growth was observed, indicating that a collection of clones had survived selection, but the majority of cells did not. Visualization of the cells by light microscopy after haematoxylin/eosin staining (FIG. 1) revealed that MCF-7 cells grew as a dense lawn of flat fibroblast-looking cells with a clear nucleus and weakly defined translucent borders. In contrast, MCF-7$_{TAX}$ cells formed large grape-like clusters of rounder cells with greater thickness, less distinct cell nuclei, and clearly defined edges for each cluster. Clear spaces between the cells were evident, forming a cobblestone-type pattern. MCF-7$_{DOX}$ cells also grew as clusters of cells with clearly defined edges for some clusters. Cell shape was very irregular and the spacing between cells varied considerably. There were often large spaces between cells. These observations suggest that selection for paclitaxel or doxorubicin resistance results in distinct changes in cell morphology and cell adhesion, consistent with recent reports that cell adhesion may be a key determinant of de novo multidrug resistance in tumor cells.

To verify that the drug-resistant cell lines were genetically related to the parental MCF-7 cell line, cells were examined using a variety of histological and immunocytochemical techniques. As shown in Table I, all cell lines formed intercellular lumens in culture and produced mucous (as indicated by positive mucicarmine and PAS staining). Such properties are consistent with all cell lines being breast adenocarcinomas. Moreover, the location and level of expression of a wide variety of tumor marker proteins were highly similar amongst the three cell lines (Table I). In addition, independent cDNA microarray experiments performed on thirteen RNA preparations extracted from each of the three cell lines indicated that the expression of >99% of 20,700 genes examined varied by less than two-fold amongst the cell lines. Taken together, these observations indicate that the MCF-7, MCF-7$_{TAX}$, and MCF-7$_{DOX}$ cell lines are genetically related (isogenic). Consequently, comparisons across the cell lines are possible. Since the drug-resistant cell lines obtained were comprised of a collection of drug-resistant clones (rather than a single clonal isolate), differences observed between the cell lines are likely a consequence of selection for growth in the presence of a particular drug, rather than selection for a particular clone within the population.

Example 2

MCF-7$_{TAX}$ Cells Exhibit Strong Resistance to Taxanes with Minimal Cross-Resistance to Doxorubicin

Figure 2:
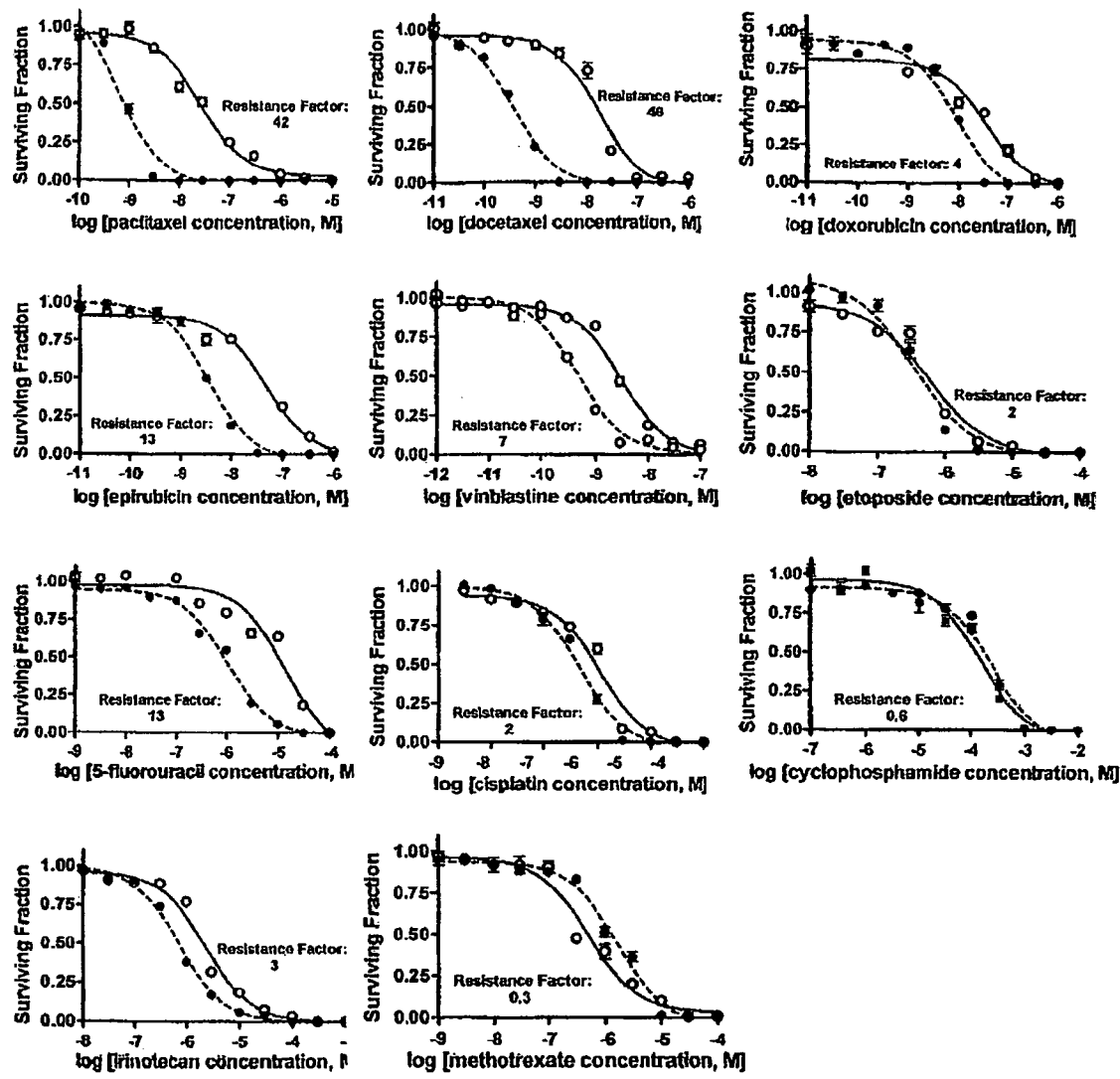
FIG. 2 shows the comparison of sensitivity of MCF-7 and MCF-7$_{TAX}$ cells to a variety of chemotherapeutic agents. MCF-7 cells (dashed line) and MCF-7$_{TAX}$ cells (solid line) were incubated with varying concentrations of a variety of chemotherapy agents in clonogenic assays as described in Materials and Methods. The percentage of surviving cells (relative to a drug-free control culture) was then determined for each concentration. The resistance factor (ratio of the IC$_{50}$ for MCF-7$_{TAX}$ cells divided by the IC$_{50}$ for MCF-7 cells) was then computed for each drug. Each curve is representative of a minimum of two experiments.

Upon verification of the isogenicity of the cell lines, we then examined their sensitivity to a wide variety of chemotherapeutic agents. As shown in FIG. 2, MCF-7$_{TAX}$ cells, as expected, were highly resistant to paclitaxel. The concentration of paclitaxel required to kill or inhibit the growth of 50% of cells (the IC$_{50}$) was 42-fold higher for drug-resistant MCF-7$_{TAX}$ cells compared to drug-sensitive MCF-7 cells. Not surprisingly, MCF-7$_{TAX}$ cells were equally resistant to another taxane (docetaxel) where its resistance factor (the ratio of the IC$_{50}$ for the drug-resistant cell line over the IC$_{50}$ for the wildtype cell line) was 46. Interestingly, MCF-7$_{TAX}$ cells showed little to moderate cross-resistance to the anthracyclines (resistance factors of approximately 4 and 13 for doxorubicin and epirubicin, respectively). Very little to no cross-resistance was found for a number of chemotherapy agents with varying modes of action, including etoposide, cisplatin, cyclophosphamide, irinotecan, and methotrexate. Interestingly, a surprising 13-fold cross-resistance of MCF-7$_{TAX}$ cells to 5-fluorouracil was observed. The mechanism responsible for this cross-resistance is not known, although DNA microarray analysis of the cell lines in our laboratory has shown that YES2 (a gene previously implicated in 5-fluorouracil resistance in cells) is highly elevated in MCF-7$_{TAX}$ cells[5].

Example 3

MCF-7$_{DOX}$ Cells Exhibit Profound Cross-Resistance to Microtubule-Targeting Drugs which Far Exceeds their Resistance to Doxorubicin

Figure 3:
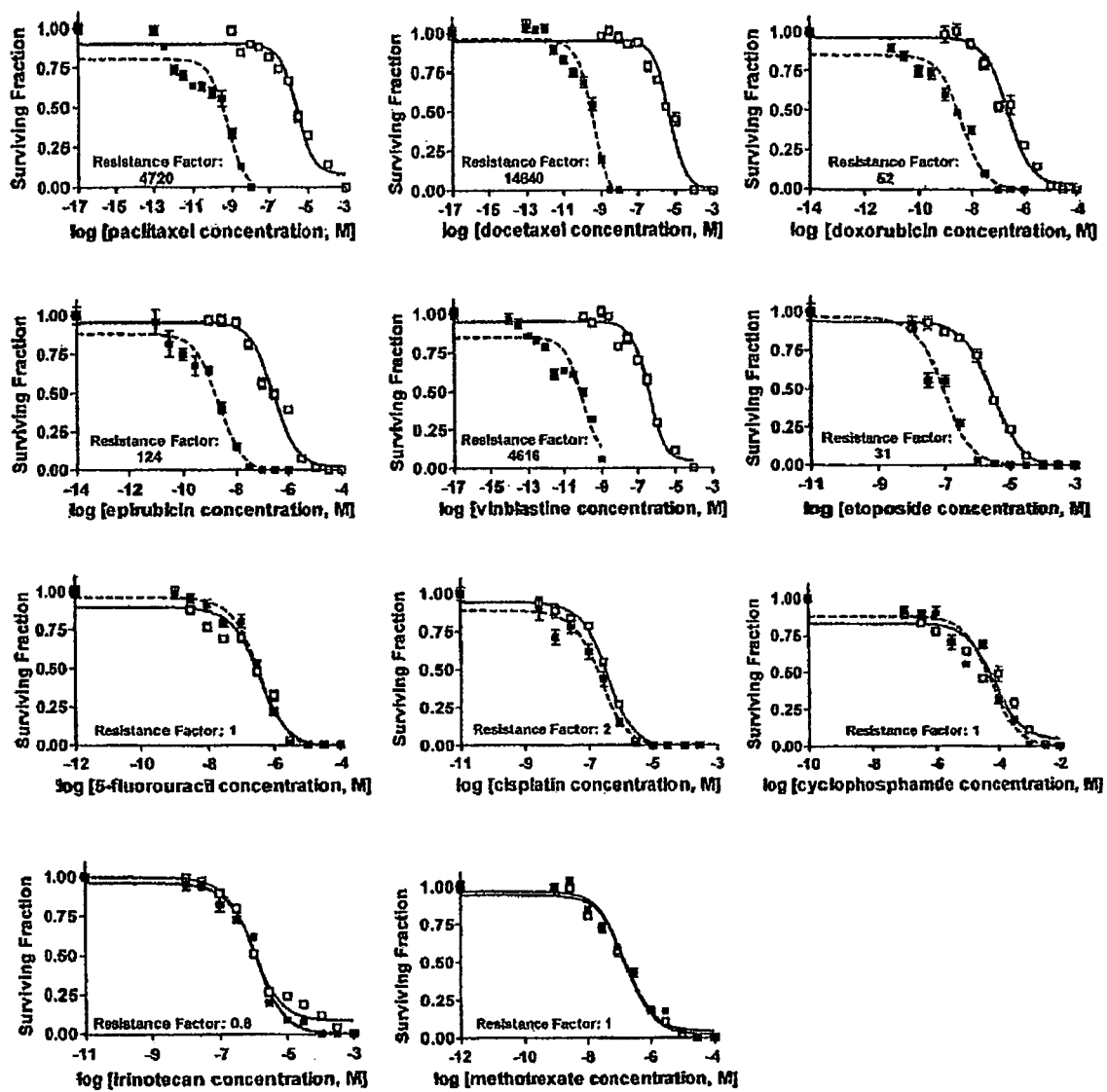
FIG. 3 shows the comparison of sensitivity of MCF-7 and MCF-7$_{DOX}$ cells to a variety of chemotherapeutic agents. MCF-7 cells (dashed line) and MCF-7$_{DOX}$ cells (solid line) were incubated with varying concentrations of a variety of chemotherapy agents in clonogenic assays as described in Materials and Methods. The percentage of surviving cells (relative to a drug-free control culture) was then determined for each concentration. The resistance factor (ratio of the IC$_{50}$ for MCF-7$_{DOX}$ cells divided by the IC$_{50}$ for MCF-7 cells) was then computed for each drug. Each curve is representative of a minimum of two experiments.

The sensitivity of MCF-7$_{DOX}$ cells to the same series of chemotherapy agents described above was also examined. As expected, MCF-7$_{DOX}$ cells were highly resistant to doxorubicin (FIG. 3). The degree of resistance (52-fold) was in a similar range to that of MCF-7$_{TAX}$ cells for paclitaxel. Cross-resistance to another anthracycline (epirubicin) was even higher for the cell line (124-fold). A surprising finding, however, was the extremely large cross-resistance which the MCF-7$_{DOX}$ cells exhibited for the taxanes. This level of cross-resistance (4,700-fold for paclitaxel and 14,600-fold for docetaxel) far exceeded resistance to doxorubicin (the drug to which MCF-7 cells were exposed in order to obtain the MCF-7$_{DOX}$ cell line). Interestingly, MCF-7$_{DOX}$ cells also had very strong cross-resistance (approximately 4600-fold) to another microtubule-targeting drug (vinblastine), showing that selection of breast tumor cells for resistance to doxorubicin has the capacity to generate cells highly resistant to a variety of microtubule-targeting drugs. Significant cross-resistance (31-fold) to etoposide was also observed for MCF-7$_{DOX}$ cells. In contrast, sensitivity of MCF-7$_{DOX}$ cells to a variety of other chemotherapy agents (5-fluorouracil, cisplatin, cyclophosphamide, irinotecan, and methotrexate) was similar to wildtype MCF-7 cells. Taken together, our observations with MCF-7$_{TAX}$ and MCF-7$_{DOX}$ cells showed that: a) selection of breast tumor cells for resistance to a specific chemotherapy agent results in drug-specific changes in the sensitivity of these cells to chemotherapy drugs, and b) the degree of cross-resistance can exceed resistance to the agent to which cells were exposed during selection. Moreover, our observations show that selection of breast tumor cells for resistance to doxorubicin has the capacity to induce a very strong cross-resistance to the taxanes. In contrast, tumor cells selected for resistance to paclitaxel (MCF-7$_{TAX}$ cells) exhibited only mild cross-resistance to the anthracyclines (particularly doxorubicin) (compare FIGS. 2 and 3). These observations show that paclitaxel and doxorubicin differ significantly in their ability to induce cross-resistance to each other and to other drugs.

Example 4

MCF-7$_{TAX}$ Cells Accumulate Less Doxorubicin and Paclitaxel than Wildtype MCF-7 Cells

Figure 4:
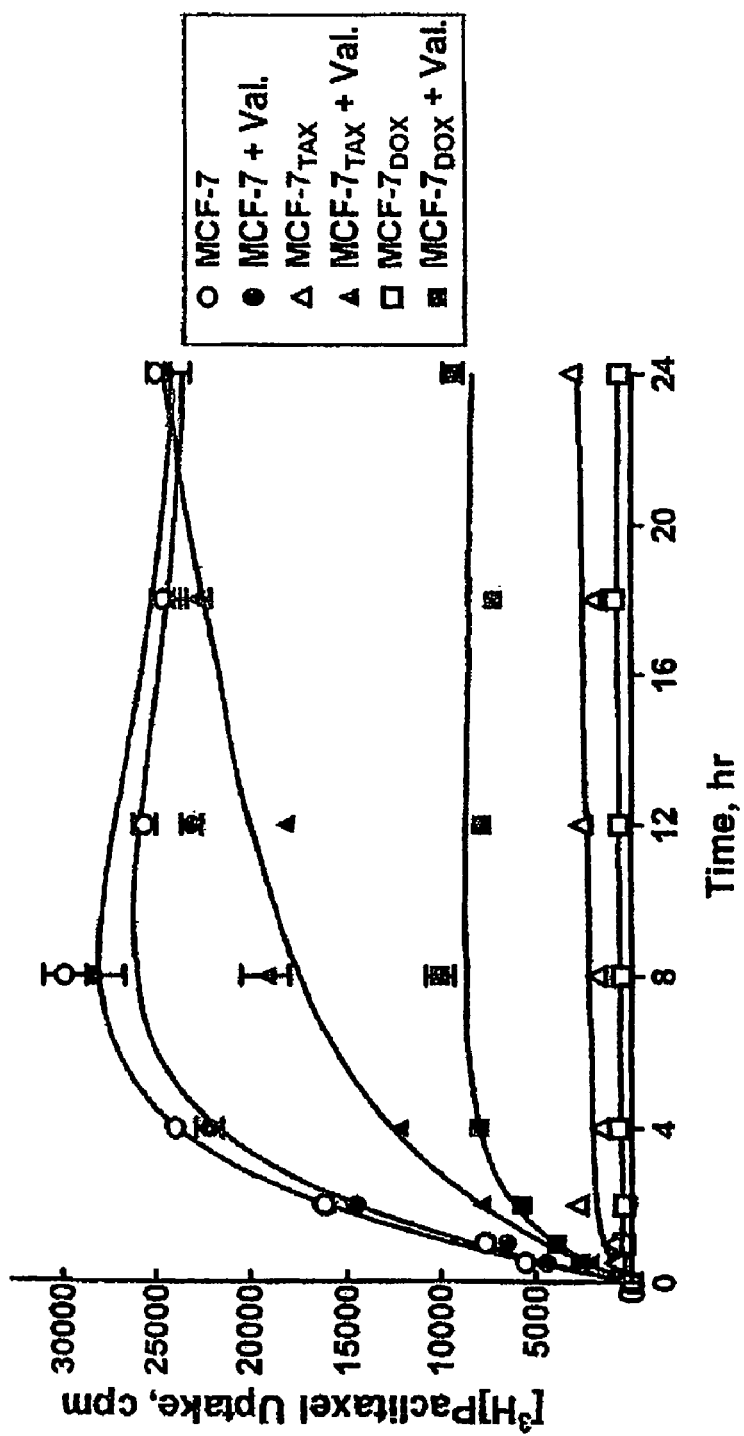
FIG. 4 illustrates the rate of influx of radiolabeled paclitaxel into MCF-7 cells (circular symbols), MCF-7$_{TAX}$ cells (triangular symbols), and MCF-7$_{DOX}$ cells (square symbols) in the absence (open symbols) or presence (closed symbols) of the P-gp inhibitor valspodar. Drug uptake was measured using liquid scintillation spectrometry as described in Materials and Methods. Values are plotted ± standard error. This figure is representative of three separate experiments.
Figure 5:
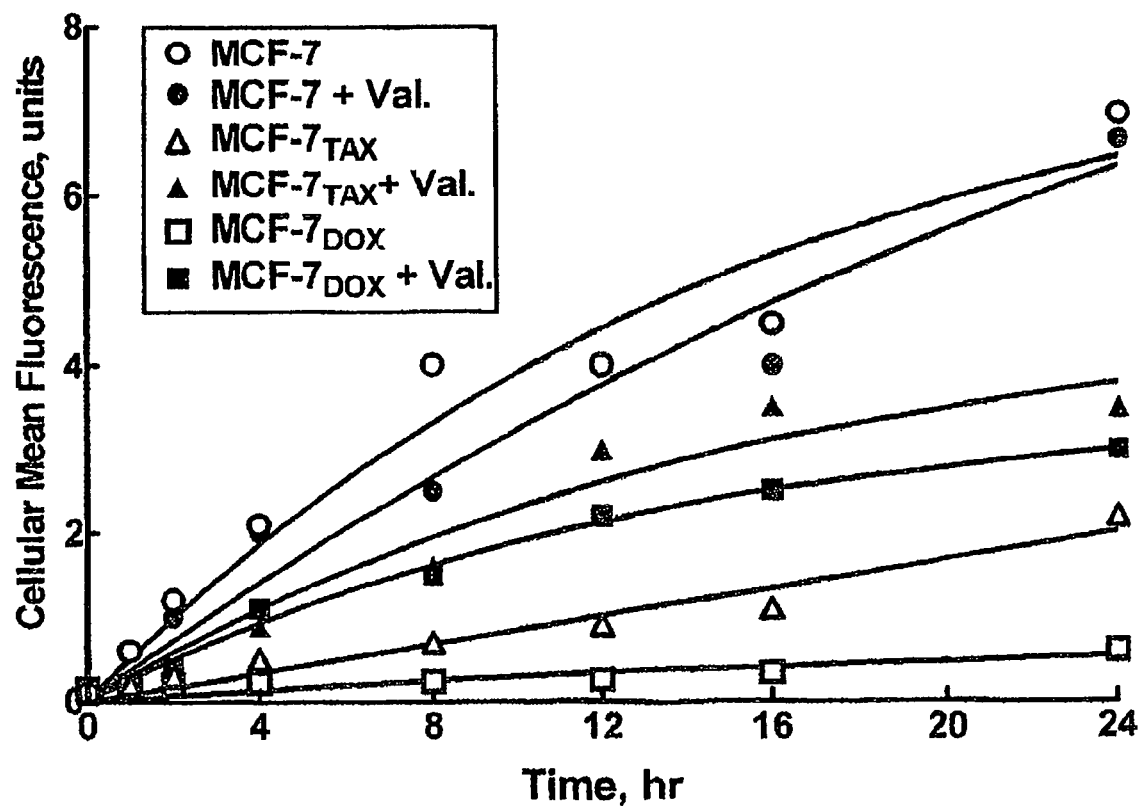
FIG. 5 illustrates the rate of influx of doxorubicin into MCF-7 cells (circular symbols), MCF-7$_{TAX}$ cells (triangular symbols), and MCF-7$_{DOX}$ cells (square symbols) in the absence (open symbols) or presence (closed symbols) of the P-gp inhibitor valspodar. Drug uptake was measured by flow cytometry as described in Materials and Methods. This figure is representative of three separate experiments.

To assess the nature of the resistance mechanisms for paclitaxel and doxorubicin in the drug-resistant cell lines, we first examined the amount of radiolabeled paclitaxel (10 nM), radiolabeled 5-Fluorouracil (1 µM), and doxorubicin (2 µM) taken up by MCF-7 and MCF-7$_{TAX}$ cells upon reaching steady state as described in Materials and Methods. As shown in FIGS. 4 and 5, MCF-7$_{TAX}$ cells accumulated substantially lower amounts of both paclitaxel and doxorubicin, which may help explain the cell line's reduced sensitivity to both of these chemotherapy agents. In 24 hours, the cells took up 87.3% less paclitaxel than wildtype cells (FIG. 4). Doxorubicin accumulation was also affected, with MCF-7$_{TAX}$ cells exhibiting 68.6% of the uptake observed in MCF-7 cells (FIG. 5). Taken together, these findings suggest that resistance to paclitaxel and doxorubicin in MCF-7$_{TAX}$ cells stems from a defect in drug accumulation. A comparison of the degree of reduced drug accumulation for paclitaxel and doxorubicin in MCF-7$_{TAX}$ cells could not be made, since the concentrations of drugs used in the uptake studies were not equimolar. Nevertheless, the drug accumulation defects in MCF-7$_{TAX}$ and MCF-7$_{DOX}$ cells were drug-specific, since the amount of [$^{14}$C]5-Fluorouracil taken up by MCF-7$_{TAX}$ and MCF-7$_{DOX}$ cells was similar to that observed for MCF-7 cells over a 24 hour period (data not shown). This was despite the fact that the doxorubicin concentration used in the uptake assays exceeded 5-Fluorouracil by two-fold. Since both paclitaxel and doxorubicin are substrates for P-glycoprotein, while 5-Fluorouracil is not, our data also suggests that P-glycoprotein may, at least in part, play a role in the reduced drug accumulation observed in MCF-7$_{TAX}$ and MCF-7$_{DOX}$ cells.

Example 5

MCF-7$_{DOX}$ Cells Exhibit Dramatically Reduced Paclitaxel Accumulation, which Exceeds that of Doxorubicin

We also compared the amount of paclitaxel and doxorubicin taken up by MCF-7 and MCF-7$_{DOX}$ cells at steady state (FIGS. 4 and 5). As expected, accumulation of doxorubicin was highly reduced in MCF-7$_{DOX}$ cells compared to MCF-7 cells (by 91.4%) (FIG. 5). However, a surprising finding was that the amount of paclitaxel taken up by MCF-7$_{DOX}$ cells was even lower than that for doxorubicin. In 24 hours, MCF-7$_{DOX}$ cells accumulated only 2.5% of the paclitaxel that MCF-7 cells accumulated during the same time period (FIG. 4). Thus, paclitaxel uptake is essentially blocked in MCF-7$_{DOX}$ cells and this may help explain the dramatic cross-resistance to the taxanes exhibited by MCF-7$_{DOX}$ cells in our clonogenic assays. Taken together, our findings show that selection of breast tumor cells for resistance to doxorubicin has the capacity to result in the generation of cells highly cross-resistant to the taxanes. This resistance appears, at least in part, to be the result of a strong reduction in the ability of cells to accumulate paclitaxel.

Example 6

Figure 6A:
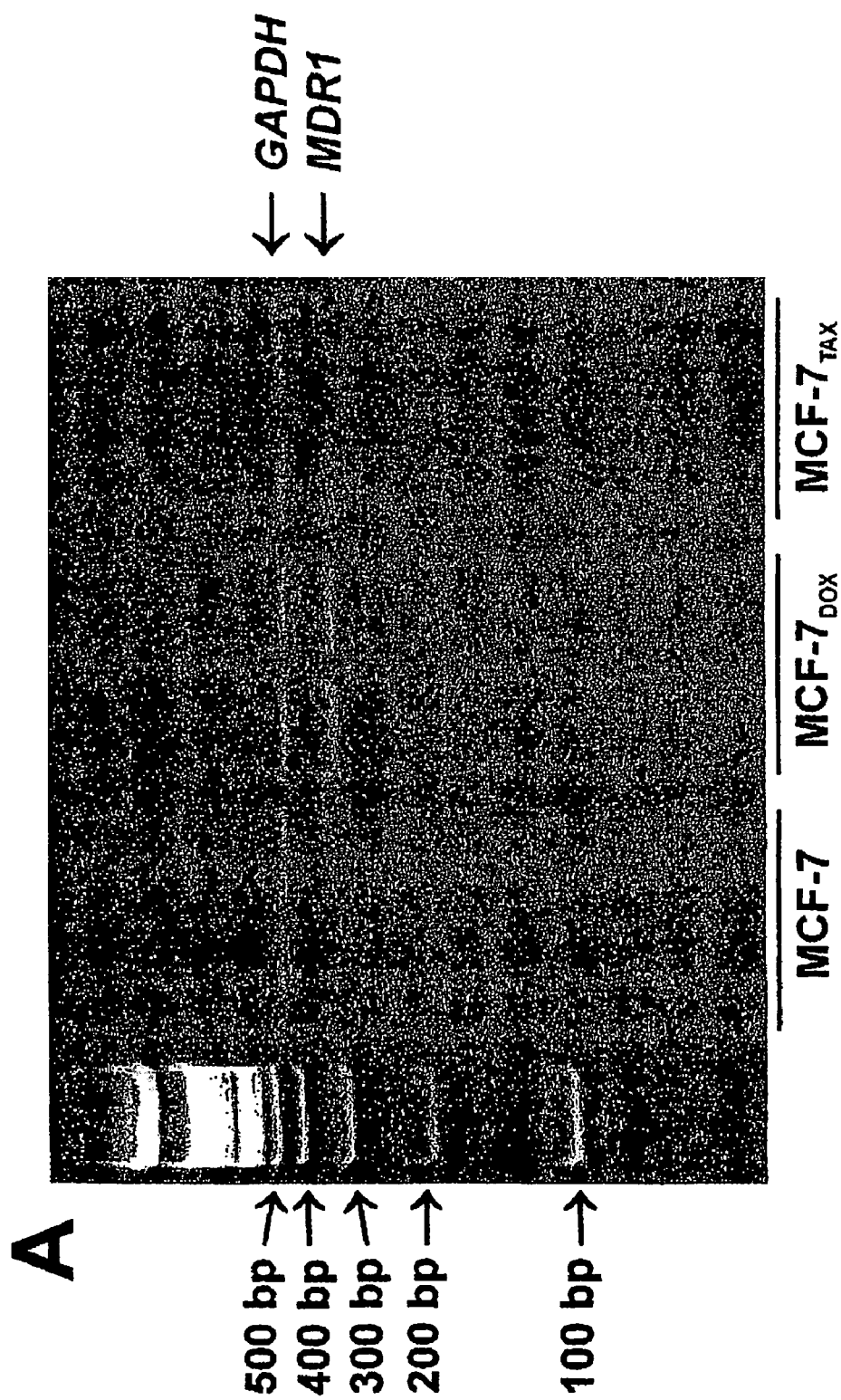
FIG. 6 illustrates: A) Expression of P-gp (MDR1) and glyceraldehyde-3-phosphate dehydrogenase (GAPDH) mRNA expression in MCF-7, MCF-7$_{TAX}$, and MCF-7$_{DOX}$ cells as measured by RT-PCR. Positions of the amplified MDR1 and GAPDH cDNA fragments are indicated with arrows. This figure is representative of three separate experiments. B) Expression of P-gp protein in the cells was also measured by flow cytometry using the P-gp-specific antibody MRK16 and a fluorescein-conjugated anti-IgG secondary antibody. Cells were considered P-gp positive if their fluorescence exceeded the maximum fluorescence of an isotypic control primary antibody (0.9 fluorescence units).
Figure 6B:
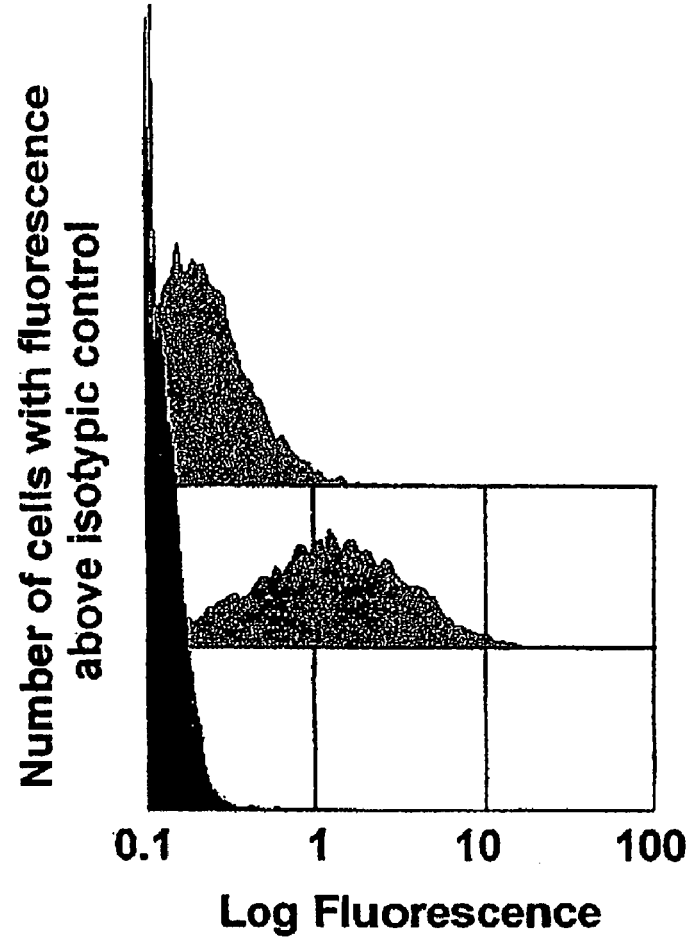

Role of P-gp in Resistance to Paclitaxel and Doxorubicin in MCF-7$_{TAX}$ and MCF-7$_{DOX}$ Cells Since both doxorubicin and paclitaxel are known substrates of the drug transporter P-gp, it is possible that P-gp may play a role in the observed resistances to doxorubicin and paclitaxel. To address this hypothesis, RT-PCR analysis was conducted on RNA extracted from MCF-7, MCF-7$_{TAX}$ and MCF-7$_{DOX}$ cells using primers specific for the MDR1 (P-gp) gene or for a "housekeeping" gene glyceraldehyde-3-phosphate dehydrogenase (GAPDH) as an internal control. As shown in FIG. 6A, dramatically higher levels of MDR1 mRNA were detected by RT-PCR in both MCF-7$_{TAX}$ and MCF-7$_{DOX}$ cells compared to wildtype cells (FIG. 6A). In contrast, GAPDH mRNA levels appeared similar in each of the cell lines. Consistent with the RT-PCR data, the amount of P-gp on the surface of cells (as detected by flow cytometry with a P-gp-specific antibody) was also substantially higher in both MCF-7$_{TAX}$ and MCF-7$_{DOX}$ cells compared to wildtype MCF-7 cells (FIG. 6B). Interestingly, both approaches also suggest that induction of P-gp expression was highest in MCF-7$_{DOX}$ cells compared to MCF-7$_{TAX}$ cells. This may, in part, explain why MCF-7$_{DOX}$ cells exhibited greater resistance to a wider number of chemotherapy drugs tested.

To assess whether other pathways (besides the induction of P-gp gene expression) played a role in drug resistance in the MCF-7$_{TAX}$ and MCF-7$_{DOX}$ cell lines, we examined whether preincubation of the cell lines with the P-gp inhibitor valspodar could fully restore drug sensitivity. Valspodar has been shown to be effective in restoring sensitivity to both doxorubicin and paclitaxel and inhibits P-gp function by blocking the ability of the molecule to bind drugs. As shown in FIG. 7A, preincubation with 2 µM valspodar fully restored the sensitivity of MCF-7$_{TAX}$ cells to paclitaxel such that the cells were indistinguishable from wildtype cells (MCF-7). Correspondingly, paclitaxel accumulation in MCF-7$_{TAX}$ cells was also fully restored by valspodar after 24 hours of drug accumulation (FIG. 4). Interestingly, the smaller cross-resistance of MCF-7$_{TAX}$ cells to doxorubicin was essentially unaffected by valspodar (FIG. 7B), despite valspodar's ability to partially restore doxorubicin accumulation in MCF-7$_{TAX}$ cells (FIG. 5). Cellular sensitivity of MCF-7$_{DOX}$ cells to both paclitaxel and doxorubicin was significantly but not completely restored by 2 µM valspodar (FIGS. 7C-7D). Increasing the concentration of valspodar to 10 µM in the medium had no additional killing effect (data not shown) and valspodar had no effect of 5-fluorouracil sensitivity in MCF-7 cells.

Example 7

Figure 8:
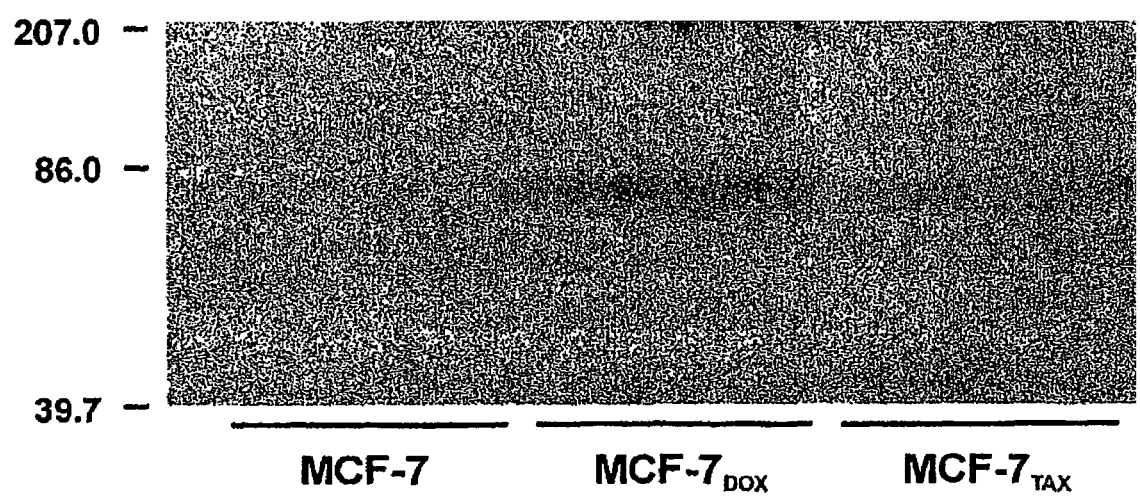
FIG. 8 shows the levels of the breast cancer resistance protein (BCRP) in MCF-7, MCF-7$_{TAX}$, and MCF-7$_{DOX}$ cells as measured by immunoblotting experiments. Protein extracts from isolated membrane preparations from the cell lines were run on SDS polyacrylamide gels, transferred to nitrocellulose membranes, and probed with an anti-BCRP monoclonal antibody as described in Materials and Methods. The molecular weights of standard proteins are depicted to the left of the blot. The figure is representative of two experiments.

Possible Role of the Breast Cancer Resistance Protein and Caspase-9 in Resistance to Paclitaxel or Doxorubicin The inability of valspodar to fully re-establish sensitivity to doxorubicin in MCF-7$_{TAX}$ cells or sensitivity to both paclitaxel and doxorubicin in MCF-7$_{DOX}$ cells suggests that, in addition to P-gp over expression, other mechanisms of drug resistance are likely present in the cell lines described herein. To assess this, we examined by immunoblotting the expression level of other proteins that have been implicated in drug resistance in biological systems. One possible candidate would be the breast cancer resistance protein (BCRP), a 655 amino acid "half transporter" (type ABCG2) which forms dimers to produce an active complex capable of transporting mitoxantrone and has been associated with resistance to anthracyclines, topotecan, and SN38 (irinotecan), but not taxane resistance. As shown in FIG. 8, western blotting of membrane extracts from MCF-7, MCF-7$_{TAX}$, and MCF-7$_{DOX}$ using a BCRP antibody revealed a single protein on immunoblots, which was significantly expressed in MCF-7$_{DOX}$ cells, but not in MCF-7 cells. The molecular weight of this protein on immunoblots was between 39.7 and 86 kDa, with the band residing closer to the 86 kDa marker protein. Using the sequence reported by Doyle and colleagues [1] and a protein molecular weight calculator found at http://scansite.mit.edu/proteincalc.html, BCRP would be expected to have a molecular weight of 72.3 to 72.9 kDa, reasonably consistent with the position of the band detected on immunoblots.

As mentioned previously, drug resistance in tumor cells can involve a repression in the ability of chemotherapy drugs to induce apoptosis in cells. We therefore surveyed the levels of various caspases involved in apoptosis regulation in MCF-7, MCF-7$_{TAX}$, and MCF-7$_{DOX}$ cells with or without prior treatment with paclitaxel or doxorubicin. FIG. 9A depicts an immunoblotting experiment where proteins from two independent whole cell extracts of MCF-7, MCF-7$_{TAX}$ and MCF-7$_{DOX}$ cells (treated with or without 9 nM doxorubicin) were resolved by electrophoresis, transferred to nitrocellulose, and probed with a caspase-9-specific antibody. As shown in FIG. 9A, MCF-7 cells, when treated with doxorubicin, exhibited elevated levels of the "pro" (uncleaved) form of caspase-9. This observation is consistent with observations in human multiple myeloma cells where doxorubicin was also found to upregulate procaspase-9. In contrast, paclitaxel had no effect on procaspase-9 levels (data not shown), suggesting that this upregulation was drug-specific. What is also noteworthy is that untreated MCF-7$_{DOX}$ cells possess considerably lower levels of procaspase-9 than MCF-7 or MCF-7$_{TAX}$ cells (FIG. 9A), suggesting a correlation between the downregulation of procaspase-9 expression and doxorubicin resistance in breast tumor cells. Consistent with this hypothesis, we observed that, even in the presence of doxorubicin, cellular levels of procaspase-9 were clearly lower in doxorubicin-resistant MCF-7$_{DOX}$ cells than in MCF-7 and MCF-7$_{TAX}$ cells (FIG. 9A). Taken together, the above findings suggest that the killing action of doxorubicin in breast tumor cells may be mediated by caspase-9 and that breast tumor cells may become resistant to doxorubicin, at least in part, through a reduction in cellular procaspase-9 levels. Cellular levels of procaspase-7 were also upregulated by doxorubicin treatment of MCF-7 cells (FIG. 9B), while paclitaxel treatment was without effect (data not shown). In addition, selection for resistance to paclitaxel or doxorubicin in these cells had no effect on procaspase-7 levels (FIG. 9B). These observations suggest that while the expression of a number of caspases is upregulated by doxorubicin, selection for resistance to doxorubicin may involve the specific downregulation of procaspase-9.

Paclitaxel- and doxorubicin-resistant breast tumor cell lines were generated by exposure of an identical lot of MCF-7 cells to increasing concentrations of either paclitaxel or doxorubicin in an identical manner. Cell lines resistant to doxorubicin or paclitaxel have been established by a large number of laboratories, particularly for doxorubicin. Moreover, a number of previously published studies have documented that selection of cells for resistance to either paclitaxel or doxorubicin can result in cross-resistance to both drugs. This would be expected, given that long-term treatment of a number of tumor cell lines with paclitaxel or doxorubicin can induce P-gp expression and since both drugs are known substrates of P-gp. However, in no previous study has there been a comparative assessment within the same cellular system of the relative capacities of paclitaxel and doxorubicin to induce cross-resistance to each other and to other drugs. To address this issue we established paclitaxel- and doxorubicin-resistant breast tumor cell lines (MCF-7$_{TAX}$ and MCF-7$_{DOX}$ cells, respectively). Through cDNA microarray analysis, we have determined that >99% of 20,700 genes surveyed in the MCF-7$_{TAX}$ and MCF-7$_{DOX}$ cell lines varied by <2-fold with MCF-7 cells. Table 1 illustrates identical tumor marker protein profiling amongst MCF-7, MCF-7$_{TAX}$, and MCF-7$_{DOX}$ cells. This data strongly suggests that the cell lines are isogenic. This enables a direct comparison across the cell lines and rules out differences in drug sensitivity across the cell lines, which may be due to selection for rare, genotypically distinct, drug-resistant clones within the MCF-7 cell population.

Figure 7:
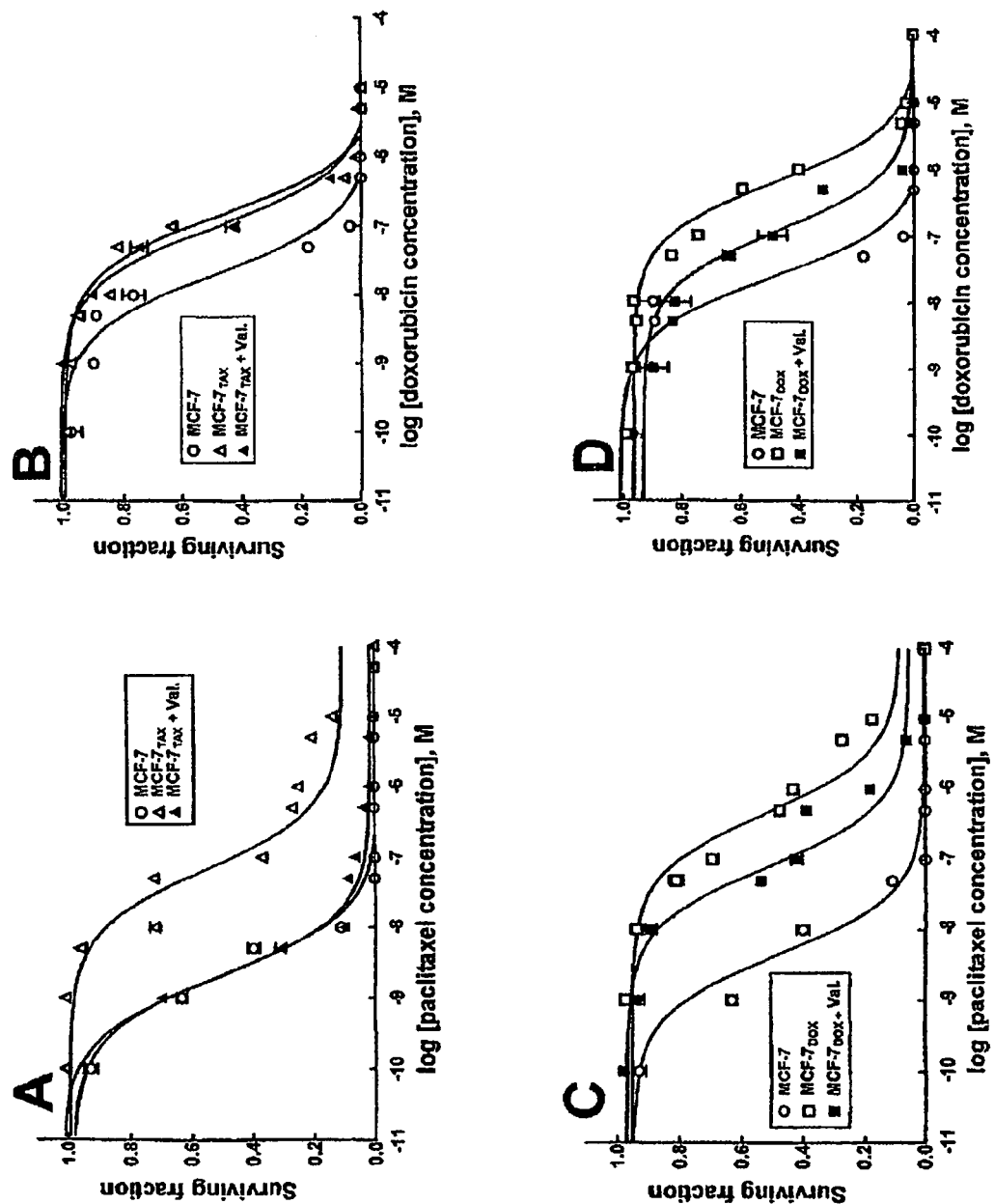
FIG. 7 illustrates the effect of the P-gp inhibitor valspodar on the sensitivity of MCF-7$_{TAX}$ cells and MCF-7$_{DOX}$ cells to killing by paclitaxel or doxorubicin. MCF-7$_{TAX}$ cells (triangular symbols) and MCF-7$_{DOX}$ cells (square symbols) were incubated with varying concentrations of paclitaxel (panels A and C) or doxorubicin (panels B and D) for 24 hours with (closed symbols) or without (open symbols) valspodar. Cell survivability was then assessed in clonogenic assays as described in Materials and Methods. The percentage of surviving cells (relative to a drug-free control culture) was then determined for each concentration. Each panel is representative of a minimum of three experiments.

Selection of MCF-7 breast tumor cells for resistance to doxorubicin (MCF-7$_{DOX}$ cells) generated a population of cells which were >4,000-fold cross-resistant to paclitaxel, while an identical selection of cells for resistance to paclitaxel (MCF-7$_{TAX}$ cells) generated a population of cells with only slight (4-fold) cross-resistance to doxorubicin. The 42-fold resistance of MCF-7$_{TAX}$ cells to paclitaxel appears to be fully the result of decreased drug accumulation, since P-gp expression is upregulated in this cell line (FIG. 6), paclitaxel accumulation in MCF-7$_{TAX}$ cells is 90% lower relative to MCF-7 cells (FIG. 4) and drug sensitivity is fully restored when MCF-7$_{TAX}$ cells are treated with an inhibitor of P-gp (FIG. 7).

A number of apparent discrepancies between drug accumulation and drug cytotoxicity were observed. For example, MCF-7$_{TAX}$ cells exhibited only a small (4-fold) cross resistance to doxorubicin (FIG. 2), despite having significantly lower rates of doxorubicin accumulation relative to wildtype MCF-7 cells (FIG. 5). Another apparent discrepancy relates to valspodar's ability to restore both drug accumulation and drug cytotoxicity in the cell lines used in this invention. Despite inducing a 50% restoration of doxorubicin accumulation in MCF-7$_{TAX}$ cells, valspodar had little effect on doxorubicin toxicity. This lack of concordance between the drug accumulation and drug cytotoxicity data may be explained by considering the relationship between these two parameters. It is likely that only for a narrow range of drug concentrations would there be a direct relationship between the cellular accumulation of a drug and its cytotoxicity. Above this range, changes in drug accumulation may have little effect on drug toxicity, since maximum cell killing would be achieved. Similarly, below this range, the concentration of drug may be sufficiently below its IC$_{50}$ that a further reduction in drug accumulation may have little effect on drug toxicity. In the former case, it is possible that despite considerably lower rates of doxorubicin accumulation observed for the cell line (FIG. 5), sufficient doxorubicin may have entered the MCF-7$_{TAX}$ cells to be cytotoxic. In the latter case, the additional doxorubicin accumulation induced by valspodar may have been insufficient to increase the cytotoxicity of the drug in MCF-7$_{TAX}$ cells. This may be related to the presence of additional P-glycoprotein-independent doxorubicin resistance pathways in MCF-7$_{TAX}$ cells after selection for resistance to paclitaxel. Moreover, a number of additional factors besides drug accumulation can affect a drug's cytotoxicity.

In contrast to our findings in MCF-7$_{TAX}$ cells, valspodar was able to significantly but not fully restore accumulation to paclitaxel (FIG. 4) or doxorubicin (FIG. 5) in MCF-7$_{DOX}$ cells. Similarly, a significant increase in both paclitaxel and doxorubicin cytotoxicity was observed. Thus, for MCF-7$_{DOX}$ cells, there was a concordance between valspodar's ability to restore paclitaxel and doxorubicin accumulation and its ability to restore the cytotoxicity of these two drugs. The effects of valspodar (at a 2 μM concentration) on the sensitivity of MCF-7$_{TAX}$ cells to paclitaxel and the sensitivity of MCF-7$_{DOX}$ cells to doxorubicin and paclitaxel were likely the result of its ability to block P-gp function since valspodar treatment of non-expressing MCF-7 cells had only a slight effect on cell viability at this concentration (data not shown). However, one cannot rule out a possible synergy between the killing actions of paclitaxel or doxorubicin entering the cell and valspodar.

While cross-resistances to paclitaxel in doxorubicin-resistant cell lines have been reported previously, our findings show the degree of cross-resistance to paclitaxel, docetaxel, and vinblastine which was observed upon selection of breast tumor cells for resistance to doxorubicin. The degree of resistance to these drugs in MCF-7$_{DOX}$ cells far exceeded that for doxorubicin by up to 290-fold. In contrast, little cross-resistance to doxorubicin (4-fold) was observed for paclitaxel-resistant cells. This suggests that breast tumor cells upon selection for resistance to doxorubicin may have the unique capacity to exhibit very strong cross-resistance to paclitaxel. Since paclitaxel is often used in second-line treatment after doxorubicin, this may not be ideal, and may help explain recent clinical trial data suggesting that responsiveness of patients to paclitaxel after late crossover from doxorubicin was substantially lower than that achieved by doxorubicin after late cross from paclitaxel.

Various mechanisms could account for the differences in capacity of these drugs to induce cross-resistance. As demonstrated previously, cellular accumulation of paclitaxel (FIG. 4) and doxorubicin (FIG. 5) were strongly reduced in both the MCF-7$_{TAX}$ and MCF-7$_{DOX}$ cell lines. One well-known molecule that could play a role in resistance to both doxorubicin and paclitaxel is the drug transporter P-gp, which has been shown to transport both drugs. Our data confirms that P-gp expression is, in fact, elevated in both MCF-7$_{DOX}$ and MCF-7$_{TAX}$ cells when compared to control MCF-7 cells (FIGS. 6A and 6B). Expression of P-gp, however, is considerably higher in MCF-7$_{DOX}$ cells compared to MCF-7$_{TAX}$ cells. This may account for the higher resistance to paclitaxel observed in the MCF-7$_{DOX}$ cell line (particularly since paclitaxel is an excellent substrate for P-gp). Supporting this hypothesis are the observations in this study that the P-gp inhibitor valspodar can completely and partially restore sensitivity to paclitaxel in MCF-7$_{TAX}$ and MCF-7$_{DOX}$ cells, respectively (FIGS. 7A and 7C). Restoration would be more difficult in the latter cell line, given its higher level of P-gp expression.

Figure 9:
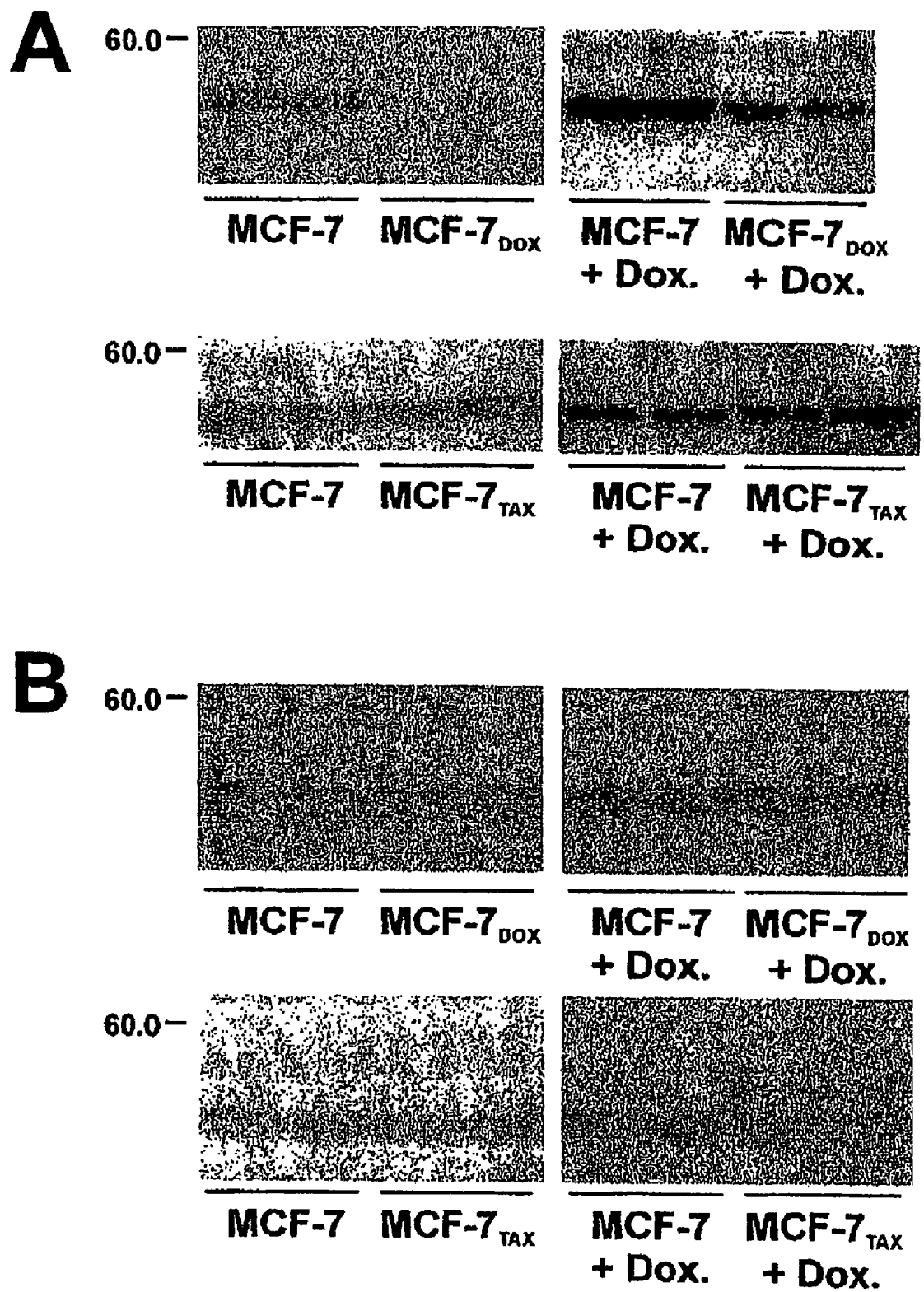
FIG. 9 shows the levels of procaspase-9 and procaspase-7 in MCF-7, MCF-7$_{TAX}$, and MCF-7$_{DOX}$ in the absence or presence of doxorubicin. Cells were treated with (right panels) or without (left panels) X nM doxorubicin for 24 hours, after which whole cell extracts of the cells were prepared. The extracts were then run on SDS polyacrylamide gels, transferred to nitrocellulose membranes, and probed with antibodies to either caspase-9 (panel A) or caspase-7 (panel B) as described in Materials and Methods. The molecular weight of a 60 kDa standard protein is indicated to the left of the blots. The figure is representative of three independent experiments.

Selection of breast tumor cells for resistance to doxorubicin appears to correlate with the downregulation of procaspase-9 (but not procaspase-7) expression (FIG. 9). In contrast, selection for resistance to paclitaxel results in no change in caspase-9 expression. Since we also show that procaspase-9 levels are upregulated in MCF-7 cells in response to doxorubicin, caspase-9 may play an important role in the cytotoxicity of doxorubicin. Consistent with this observation would be a recent study demonstrating that doxorubicin activates a mitochondria-regulated mechanism of apoptosis in MCF-7 cells involving cytochrome c release from mitochondria and activation of caspase-9. Also supporting this hypothesis is the observation that caspase-9 is activated by doxorubicin in the PA1 ovarian cell line and that expression of a dominant negative inhibitor of caspase-9 in this cell line resulted in resistance to doxorubicin cytotoxicity. However, the present inventor found that doxorubicin treatment of PA1 cells resulted in a decrease in procaspase-9 levels, likely due an ability of the drug to induce cleavage of procaspase-9. Thus, one cannot rule out differences between MCF-7 and PA1 cells in their ability to undergo drug-induced caspase-9 cleavage, which may temper conclusions derived from comparisons between the two cell lines. Nevertheless, to our knowledge, we have discovered the specific downregulation of procaspase-9 upon selection for doxorubicin resistance in tumor cells. Since caspase-9 has also been implicated in resistance to paclitaxel-induced apoptosis in HL-60 cells, it is possible that the cross-resistance to paclitaxel in MCF-7$_{DOX}$ cells may also be the result of the downregulation of procaspase-9. Given the above findings and the many previously described proteins implicated in resistance to anthracyclines and taxanes in tumor cells, it is likely that a variety of these proteins are involved in the alterations in drug accumulation and drug sensitivity observed in our study for MCF-7$_{TAX}$ and MCF-7$_{DOX}$ cells. Consequently, blockage of the expression/activity of any one particular protein may likely induce only minor changes in drug accumulation and/or drug sensitivity.

Given that downregulation of procaspase-9 accompanies resistance to doxorubicin, one may determine a patient's resistance to this drug based on a test to determine the presence of procaspase-9 within a sample from the patient. Such a test involves withdrawing a sample from the patient, such as a tissue sample from the patient's tumor, testing this sample for the presence of procaspase-9 and determining the patient's resistance to the drug based on the presence or absence of procaspase-9 relative to a predetermined level.

Valspodar has the ability to restore sensitivity to both doxorubicin and paclitaxel in drug-resistant breast tumor cells. Valspodar completely and partially restored sensitivity to paclitaxel and doxorubicin in MCF-7$_{TAX}$ cells, respectively, while having little effect on cross-resistance to doxorubicin. Valspodar also significantly restored sensitivity to both paclitaxel and doxorubicin in MCF-7$_{DOX}$ cells. This data suggests that valspodar may be useful to induce tumor sensitivity to paclitaxel in breast cancer patients who are clinically unresponsive to the drug. Since valspodar appears effective in significantly restoring responsiveness to both paclitaxel and doxorubicin in MCF-7$_{DOX}$ cells, the drug may also be of value for use after chemotherapy with doxorubicin to restore responsiveness to this agent once resistance has been established and/or to augment the response to paclitaxel after doxorubicin chemotherapy. As stated previously, only approximately one half of patients respond to paclitaxel after doxorubicin chemotherapy [2]. Valspodar has been shown to have some potential to restore clinical responsiveness to a combination of mitoxantrone, etoposide, and cytarabine in patients with refractory and relapsed acute myelogenous leukemia (AML). In a more recent study of a small clinical population, 32% of non-responsive AML patients achieved complete remission upon treatment with valspodar during chemotherapy; another 11% of these patients achieved partial remission.

It should be noted that the maximally tolerated dose for MCF-7 cells may be higher than that used in the treatment of patients with breast cancer. However, it is difficult to estimate the actual concentration of drugs to which cells within a breast tumor are exposed during chemotherapy. Drug accumulation in tumors is affected by a variety of factors besides the concentration of drug given to patients. These include the degree of vascularization of the tumor and the pharmacodynamic properties of the drug.

It is interesting to note that our findings in vitro are in agreement with recently published clinical findings, suggesting that prior exposure to doxorubicin may reduce the efficacy of paclitaxel in patients with breast tumors. This suggests that studies in vitro are useful in guiding the choice and/or order of drugs for prospective clinical trials, particularly, if the cell lines used are isogenic, allowing for comparisons across cell lines. Moreover, when incorporated with high throughput approaches such as cDNA and protein microarray analyses, these studies of isogenic cell lines have the prospect of identifying a wide variety of prospective prognostic factors which may prove highly useful in predicting tumor response to specific chemotherapy drugs.

REFERENCES

1. Doyle L A, Yang W, Abruzzo L V, Krogmann T, Gao Y, Rishi A K, Ross D D: A multidrug resistance transporter from human MCF-7 breast cancer cells. Proc Natl Acad Sci USA 95: 15665-15670, 1998.
2. Crown J. Nonanthracycline containing docetaxel-based combinations in metastatic breast cancer. Oncologist 6 Suppl 3: 17-21, 2001.

TABLE 1

| Stain/Antibody | MCF-7 | MCF-7$_{TAX}$ | MCF-7$_{DOX}$ | NCI$_{ADR}$ |
|---|---|---|---|---|
| Haematoxylin/eosin | intercellular lumens | intercellular lumens | intercellular lumens | no intercellular lumens |
| Mucicarmine | +, extracellular | +, extracellular | +, extracellular | − |
| PAS | ++, extracellular | ++, extracellular | ++, extracellular | − |
| α1 Antichymotrypsin | ++, cytoplasmic | ++, cytoplasmic | ++, cytoplasmic | − |
| Carcinoembryonic antigen | ++, cytoplasmic | ++, cytoplasmic | ++, cytoplasmic | − |
| Cytokeratin 7 | − | − | − | ND |
| Cytokeratin 20 | ++++, cytoplasmic | ++, cytoplasmic | +++, cytoplasmic | ND |
| Keratin E1A | ++++, cytoplasmic | +++++, cytoplasmic | +++++, cytoplasmic | ND |
| LMW Keratin | +++++, cytoplasmic | +++++, cytoplasmic | +++++, cytopasmic | +, cytoplasmic |
| Vimentin | +, cytoplasmic | +, cytoplasmic | +, cytoplasmic | ++++, cytoplasmic |
| Epith. Mem. Antigen | ++++, cytoplasmic | +++, cytoplasmic | +++++, cytoplasmic | +, cytoplasmic |
| S100 Protein | +, cytoplasmic | +, cytoplasmic | +, cytoplasmic | ++++, cytoplasmic |
| Estrogen Receptor | ++++, nuclear | ++++, nuclear | ++++, nuclear | ND |
| Progest. Receptor | +, nuclear | +, nuclear | +, nuclear | ND |
| Bcl-2 | ++, cytoplasmic | ++, cytoplasmic | ++, cytoplasmic | ND |
| p53 | − | +, nuclear | ++, nuclear | ++++, nuclear |
| caspase-3 | − | − | − | +++ |

The invention claimed is:

1. A method of determining an order of administration of a plurality of chemo-therapeutic drugs for killing cancerous cells to reduce the induction of drug cross-resistance in a patient, comprising the steps of:
   (a) providing a panel of cell strains obtained from the same tumor type as said cancerous cells, said panel comprising a parental strain sensitive to all of said drugs and two or more progeny strains each being resistant to a separate one of said chemotherapeutic drugs;
   (b) assessing the sensitivity of each of said progeny strains to each of said drugs relative to the drug-sensitive parental strain to thereby determine the extent of resistance of each of said strains to each of said drugs;
   (c) determining said order of administering said drugs using said sensitivity information, wherein the drug which corresponds to the strain which demonstrates the least resistance to the others of said drugs is determined to be the first to be administered while any other drug which corresponds to a strain which demonstrates a greater cross-resistance is assigned a value as a subsequent drug to be administered.

2. A method as defined in claim 1, wherein said drugs are assigned ascending values for the order of administration from the drug which corresponds to the strain which demonstrates the least cross-resistance to said drugs to the drug corresponding to the strain which demonstrates the most cross-resistance.

3. A method as defined in claim 2, wherein said values are determined by assigning a resistance factor to each of said strain/drug combination comprising the ratio of the amount of a selected drug required to kill 50% of said cells of said strain divided by the amount of said selected drug required to kill 50% of the cells of said parent strain, and generating an X by Y cross-resistance array wherein one axis represents said strains and the other axis represents each of said drugs, with the resistance factors being entered within said array for each intersection between X and Y entries, and using said array to assign said ascending values.

4. The method defined in claim 1, wherein said cancerous cells are selected from breast and uterine cancer cells.

5. The method defined in claim 1, wherein said drugs are selected from paclitaxel, doxorubicin, epirubicin, 5-fluorouracil, irinotecan, vinblastine, methotrexate, cisplatine, valspodar, cyclophosphamide, mitoxantrone, topotecan, and bisantrene.

6. A panel comprising a plurality of strains of cells selected from an isogenic cell culture obtained from a single cancerous tumor, each said strain comprising a population of isogenic cells, a first said population comprising a parental strain sensitive to a plurality of selected chemotherapeutic drugs, and at least second and third of said populations each being resistant to a different one of said drugs, each of said populations being isogenic with the others of said populations.

7. A panel as defined in claim 6, wherein said cancerous tumor is selected from breast and uterine tumors.

8. A panel as defined in claim 7, wherein said drugs are selected from paclitaxel, doxorubicin, epirubicin, 5-fluorouracil, irinotecan, vinblastine, methotrexate, cisplatine, valspodar, cyclophosphamide, mitoxantrone, topotecan, and bisantrene.

9. A method of determining an order of administration of a plurality of cytotoxic drugs for killing harmful cells to reduce the induction of drug cross-resistance in said cells, comprising the steps of:
   (a) providing an isogenic panel of cell strains obtained from the same cell type as said undesired cells, said panel comprising a parental strain sensitive to all of said drugs and two or more progeny strains each being resistant to a separate of said drugs;
   (b) assessing the sensitivity of each of said progeny strains to each of said drugs relative to the drug-sensitive parental strain to thereby determine the extent of resistance and cross-resistance of each of said strains to each of said drugs;
   (c) determining said order of administering said drugs using said sensitivity information, wherein the drug which corresponds to the strain which demonstrates the least resistance to the others of said drugs is determined to be the first to be administered while any other drug which corresponds to a strain which demonstrates a greater cross-resistance is assigned a value as a subsequent drug to be administered.

10. A method as defined in claim 9, wherein said drugs are assigned ascending values for the order of administration from the drug which corresponds to the strain which demonstrates the least cross-resistance to said drugs to the drug corresponding to the strain which demonstrates the most cross-resistance.

11. A method as defined in claim 10, wherein said values are determined by assigning a resistance factor to each of said strain/drug combination comprising the ratio of the amount of a selected drug required to kill 50% of said cells of said strain divided by the amount of said selected drug required to kill 50% of the cells of said parent strain, and generating an X by Y cross-resistance array wherein one axis represents said strains and the other axis represents each of said drugs, with the resistance factors being entered within said array for each intersection between X and Y entries, and using said array to assign said ascending values.

* * * * *

UNITED STATES PATENT AND TRADEMARK OFFICE
CERTIFICATE OF CORRECTION

PATENT NO. : 7,588,903 B2
APPLICATION NO. : 10/580507
DATED : September 15, 2009
INVENTOR(S) : Parissenti et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 448 days.

Signed and Sealed this

Twenty-first Day of September, 2010

David J. Kappos
*Director of the United States Patent and Trademark Office*

SEQUENCE LISTING

<160> NUMBER OF SEQ ID NOS: 4

<210> SEQ ID NO 1
<211> LENGTH: 20
<212> TYPE: DNA
<213> ORGANISM: Artificial
<220> FEATURE:
<223> OTHER INFORMATION: Primer

<400> SEQUENCE: 1
accacagtcc atgccatcac        20

<210> SEQ ID NO 2
<211> LENGTH: 20
<212> TYPE: DNA
<213> ORGANISM: Artificial
<220> FEATURE:
<223> OTHER INFORMATION: Primer

<400> SEQUENCE: 2
tccaccaccc tgttgctgta        20

<210> SEQ ID NO 3
<211> LENGTH: 29
<212> TYPE: DNA
<213> ORGANISM: Artificial
<220> FEATURE:
<223> OTHER INFORMATION: Primer

<400> SEQUENCE: 3
gcctggcagc tggaagacaa atacacaaa        29

<210> SEQ ID NO 4
<211> LENGTH: 32
<212> TYPE: DNA
<213> ORGANISM: Artificial
<220> FEATURE:
<223> OTHER INFORMATION: Primer

<400> SEQUENCE: 4
cagacagcag ctgacagtcc aagaacagga ct        32